(12) United States Patent
Yamaya et al.

(10) Patent No.: US 7,537,561 B2
(45) Date of Patent: *May 26, 2009

(54) ENDOSCOPE APPARATUS

(75) Inventors: Koji Yamaya, Hachioji (JP); Haruhiko Ueno, Hachioji (JP); Koji Nakamoto, Hachioji (JP); Hisao Yabe, Hachioji (JP)

(73) Assignee: Olympus Corporation, Tokyo (JP)

( * ) Notice: Subject to any disclaimer, the term of this patent is extended or adjusted under 35 U.S.C. 154(b) by 470 days.

This patent is subject to a terminal disclaimer.

(21) Appl. No.: 10/721,518

(22) Filed: Nov. 25, 2003

(65) Prior Publication Data
US 2004/0106850 A1 Jun. 3, 2004

(30) Foreign Application Priority Data

| | | | |
|---|---|---|---|
| Nov. 27, 2002 | (JP) | | 2002-344216 |
| Dec. 16, 2002 | (JP) | | 2002-364204 |
| Dec. 16, 2002 | (JP) | | 2002-364205 |
| Dec. 17, 2002 | (JP) | | 2002-365730 |

(51) Int. Cl.
*A61B 1/00* (2006.01)
(52) U.S. Cl. .............. 600/106; 600/104; 600/107; 600/129; 600/153
(58) Field of Classification Search ......... 600/104–107, 600/129, 153
See application file for complete search history.

(56) References Cited

U.S. PATENT DOCUMENTS

| | | | |
|---|---|---|---|
| 4,436,087 A | 3/1984 | Ouchi | |
| 6,071,233 A | 6/2000 | Ishikawa et al. | |
| 6,352,503 B1 * | 3/2002 | Matsui et al. | 600/104 |
| 6,458,074 B1 | 10/2002 | Matsui et al. | |
| 6,824,509 B2 * | 11/2004 | Yamaya et al. | 600/106 |
| 2003/0040657 A1 | 2/2003 | Yamaya et al. | |
| 2003/0163029 A1 * | 8/2003 | Sonnenschein et al. | 600/160 |

FOREIGN PATENT DOCUMENTS

| | | |
|---|---|---|
| JP | 48-81688 | 12/1971 |
| JP | 49-82188 | 8/1974 |
| JP | 51-53789 | 4/1976 |
| JP | 54-81690 | 6/1979 |
| JP | 03-215239 | 9/1991 |
| JP | 3-275028 | 12/1991 |
| JP | 07-008450 | 1/1995 |
| JP | 2001-212078 | 8/2001 |
| JP | 2003-210389 | 7/2003 |

* cited by examiner

*Primary Examiner*—Linda C Dvorak
*Assistant Examiner*—Matthew J Kasztejna
(74) *Attorney, Agent, or Firm*—Scully, Scott, Murphy & Presser, P.C.

(57) ABSTRACT

An edge portion of an endoscope inserting portion includes an observation optical system, a first treatment-tool oscillating base which guides, in a first direction, a first treatment tool guided via a first channel for inserting the treatment tool, and a second treatment-tool oscillating base which guides, in a second direction, a second treatment tool guided via a second channel for inserting the treatment tool. Upon endoscope treatment for the lesion portion using the first and second treatment tools which are projected from the edge openings of two first and second channels for inserting the treatment tool and which are guided by the two first and second treatment-tool oscillating bases, one of the first and second treatment tools is moved to the outside of a field of view of an endoscope image as needed.

8 Claims, 21 Drawing Sheets

ENDOSCOPE APPARATUS

This application claims benefits of Japanese Application No. 2002-365730 filed in Japan on Dec. 17, 2002, Japanese Application No. 2002-364205 filed in Japan on Dec. 16, 2002, Japanese Application No. 2002-344216 filed in Japan on Nov. 27, 2002, and Japanese Application No. 2002-364204 filed in Japan on Dec. 16, 2002, the contents of which are incorporated by this reference.

BACKGROUND OF THE INVENTION

1. Field of the Invention

The present invention relates to an endoscope apparatus which includes at least two channels for inserting a treatment tool and has a treatment-tool oscillating base which guides the treatment tool projected from the openings of the two channels for inserting the treatment tool.

2. Description of the Related Art

Recently, an endoscope apparatus is widely used for various curing which are performed by inserting an elongated inserting portion in the living body so as to observe the organ in the living body or by using a treatment tool inserted in a channel for inserting a treatment tool as needed.

In the above-mentioned endoscope apparatuses, as disclosed in Japanese Unexamined Utility Model Application Publication No. 51-53789, one endoscope apparatus has a treatment-tool oscillating base having a luminal treatment-tool inserting portion included at an edge portion of an endoscope inserting portion inserted into the living body, wherein the treatment-tool oscillating base is remotely controlled by a single operating wire and the edge of a treatment tool into which the treatment-tool inserting portion is inserted is oscillated and is guided.

Further, the efficiency of the following technology is widely recognized. That is, according to the technology, a plurality of channels for inserting a plurality of treatment tools are provided for an endoscope, the lesion portion in the living body is incised by using the endoscope in which treatment tools are inserted in the channels for inserting the treatment tool.

Furthermore, Japanese Unexamined Patent Application Publication No. 2001-212078 discloses another endoscope apparatus having a plurality of channels for inserting a treatment tool, wherein two mechanisms for standing up a clamp that stand up in different directions and treatment tools are inserted in two channels for inserting the treatment tool.

In the endoscope apparatus disclosed in Japanese Unexamined Patent Application Publication No. 2001-212078, edge opening portions of the two channels for inserting the treatment tool have the mechanisms for standing up the clamp that stand up in different directions, the treatment is performed by combining a treatment tool for grip (hereinafter, referred to as a grip clamp) inserted in one channel for inserting the treatment tool and a treatment-tool for incision (hereinafter, referred to as an incision tool) such as a needle electric knife, which is inserted in another channel for inserting the treatment tool. Specifically, the mucous membrane in the lesion or its adjacent portion is gripped and is picked up by the grip clamp and then it is incised by the incision tool.

SUMMARY OF THE INVENTION

According to the present invention, an endoscope apparatus comprises: an observation optical system which is arranged to an inserting portion; a first treatment-tool oscillating base which guides, in a first direction, a first treatment-tool guided via a first channel arranged to the inserting portion; and a second treatment-tool oscillating base which guides, in a second direction, a second treatment-tool guided via a second channel arranged to the inserting portion, wherein the end of at least one of the first and second treatment-tools guided by the first and second treatment-tool oscillating bases is guided to the outside of a field of view from the inside of an endoscope image based on an optical image obtained by the observation optical system.

DESCRIPTION OF THE PREFERRED EMBODIMENTS

Hereinbelow, a description is given of embodiments of the present invention with reference to the drawings.

First Embodiment

Figure 1:
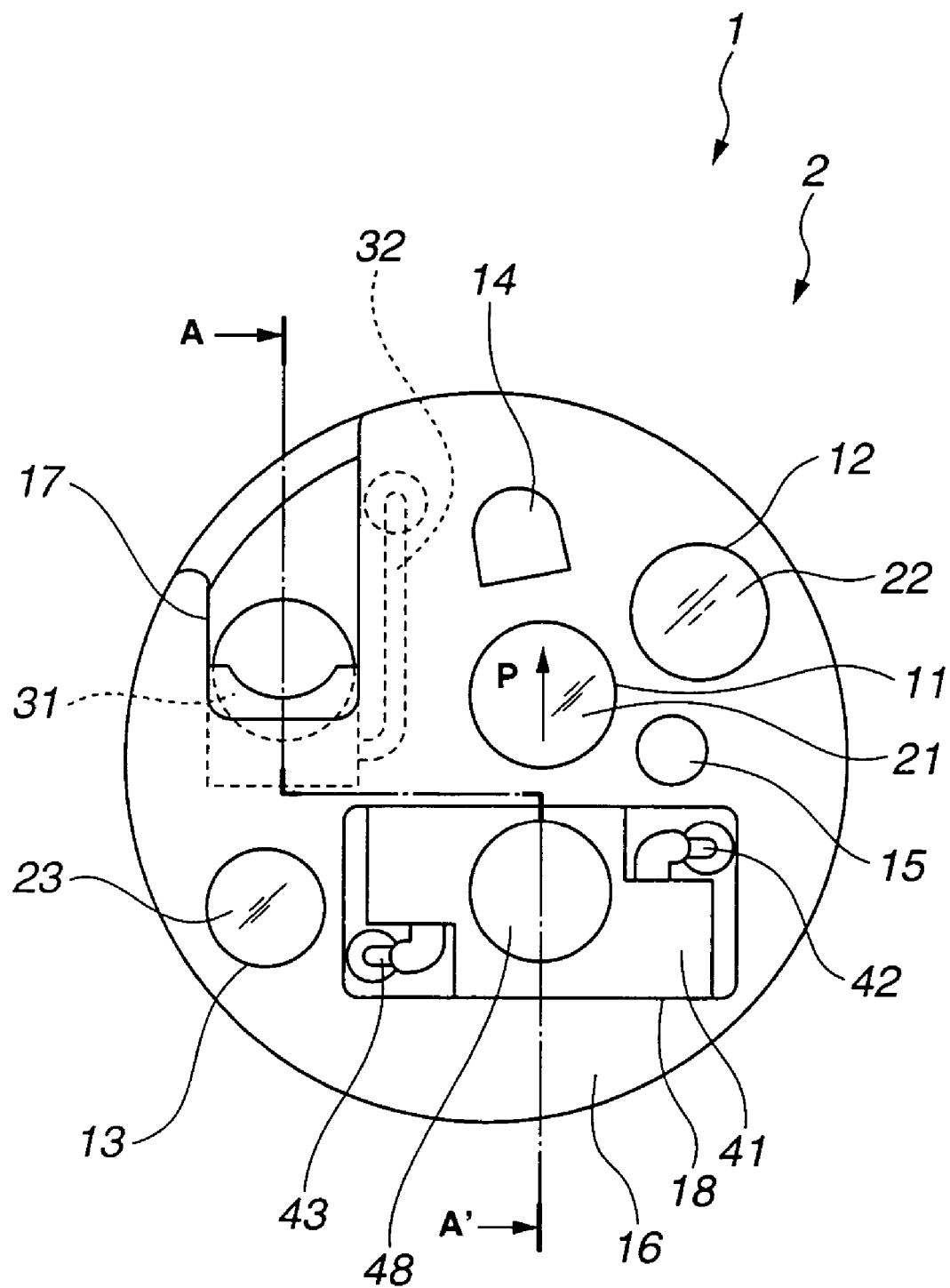
FIG. 1 is a front view of an edge portion of an endoscope inserting portion in an endoscope apparatus according to a first embodiment of the present invention.
Figure 2:
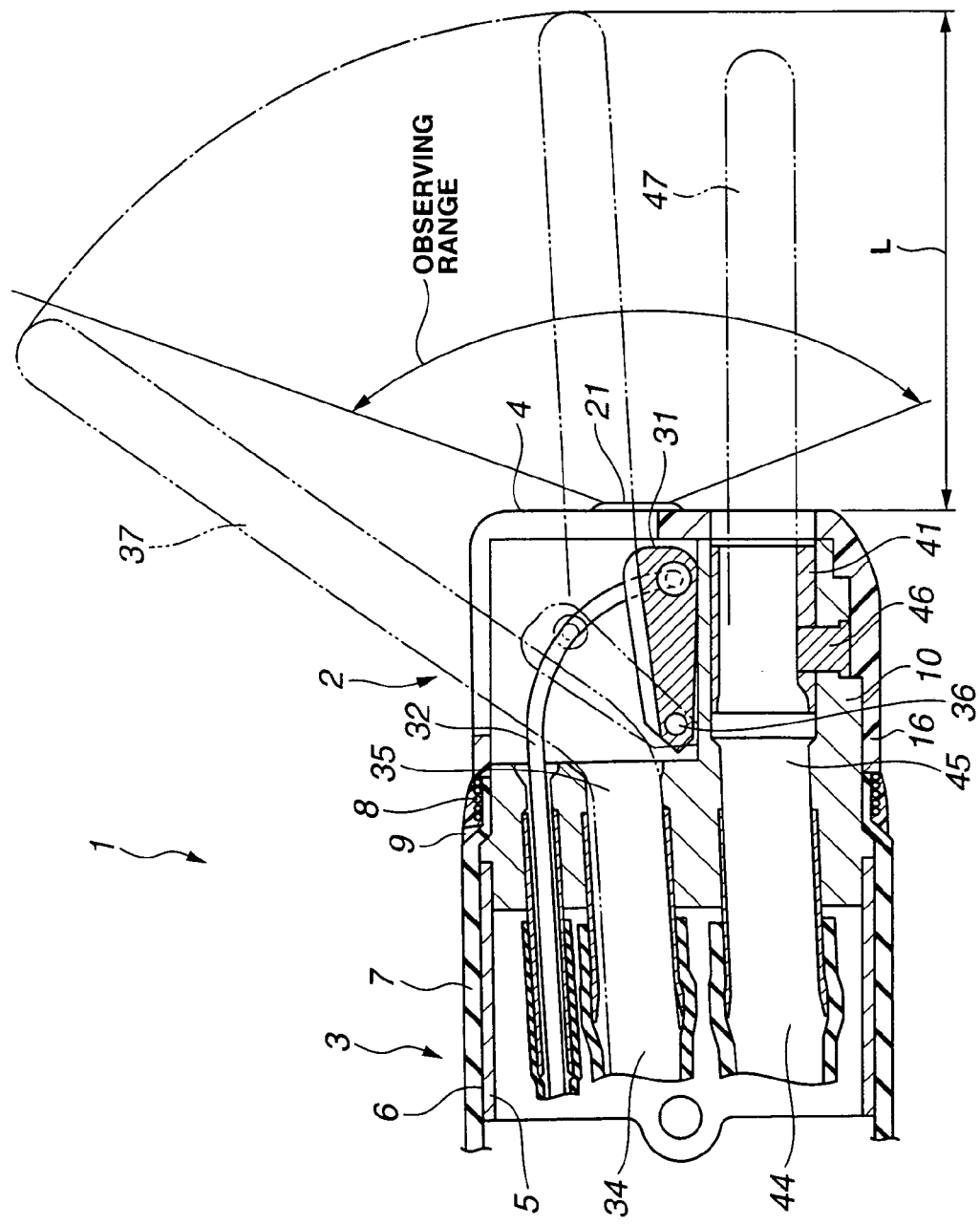
FIG. 2 is a cross-sectional view of the edge side of the endoscope inserting portion in the longitudinal direction according to the first embodiment.
Figure 3:
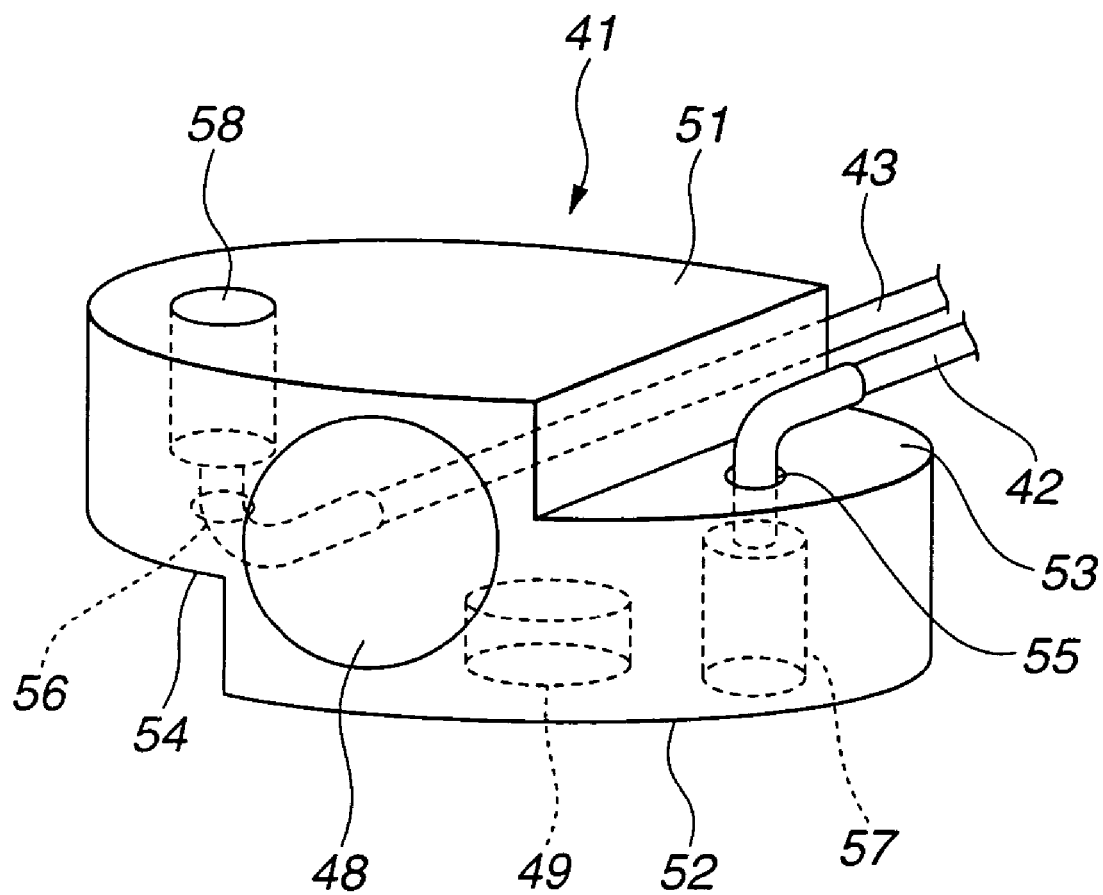
FIG. 3 is a perspective view showing, of first and second treatment-tool oscillating bases, the second treatment-tool oscillating base according to the first embodiment of the present invention.
Figure 4:
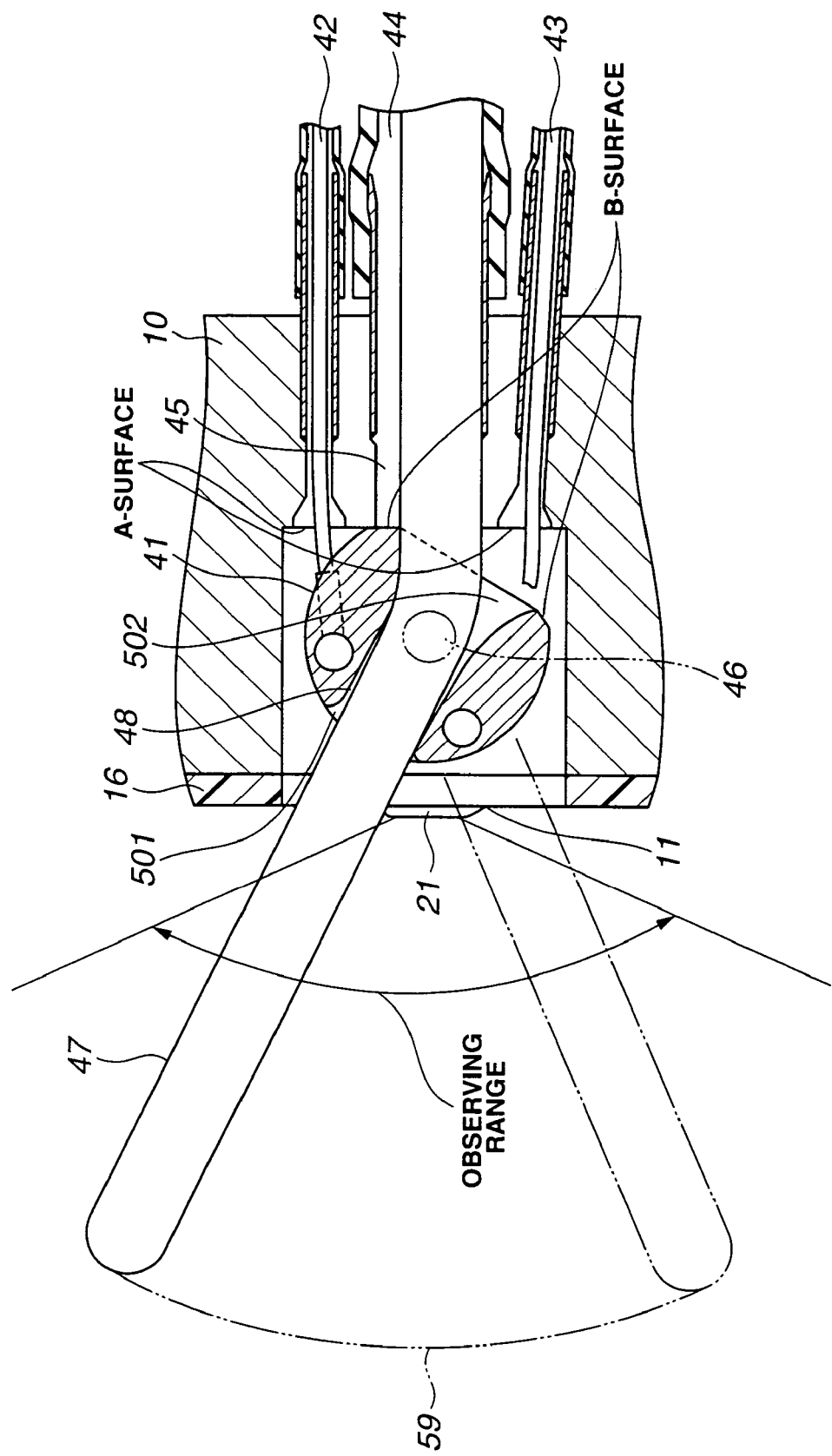
FIG. 4 is an explanatory diagram showing the motion of the second treatment-tool oscillating base and a second treatment-tool in first and second treatment-tools according to the first embodiment.
Figure 5:
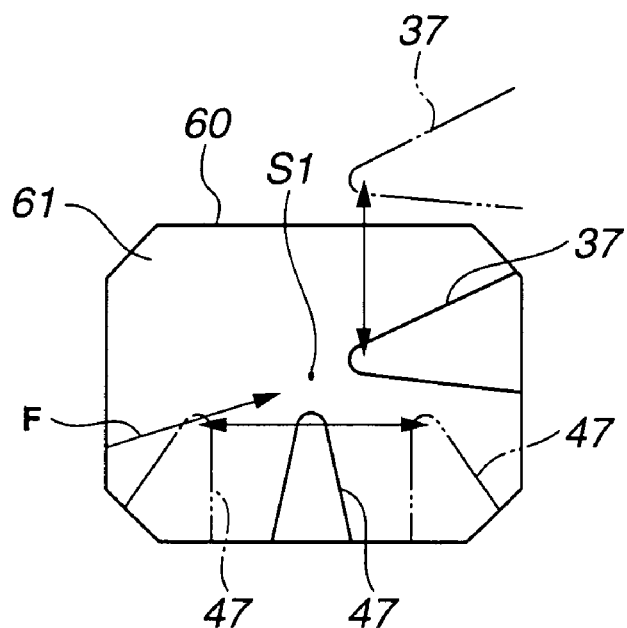
FIG. 5 is a first explanatory diagram showing a relationship between a field of view and the first and second treatment-tools according to the first embodiment.
Figure 6:
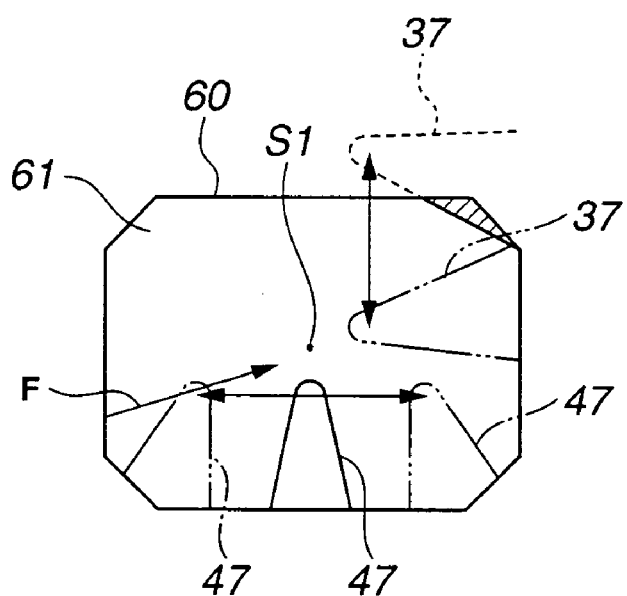
FIG. 6 is a second explanatory diagram showing the relationship between the field of view and the first and second treatment-tools according to the first embodiment.
Figure 7:
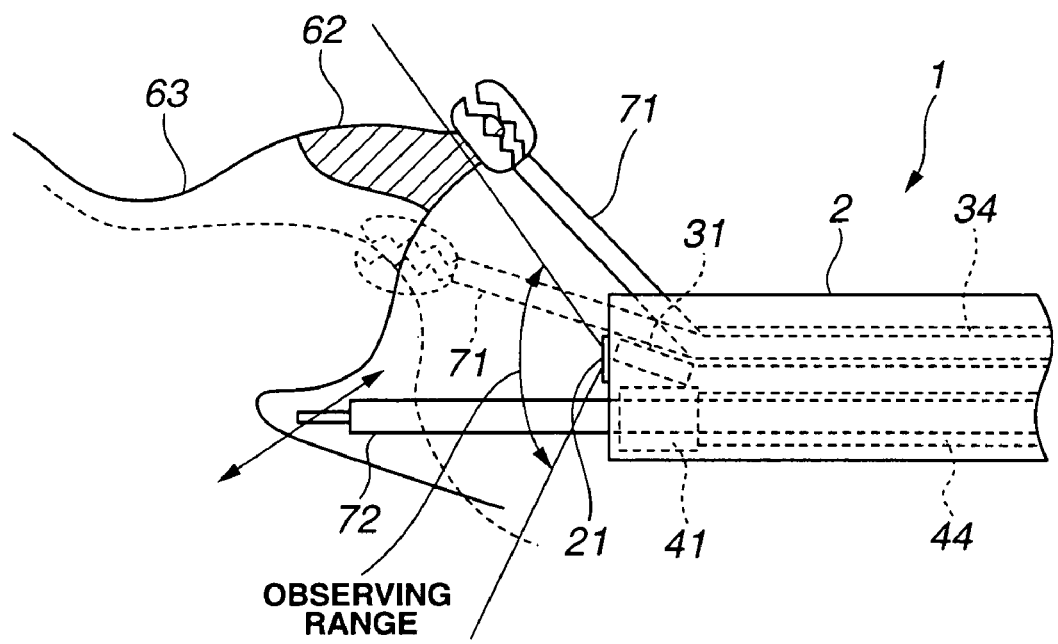
FIG. 7 is an explanatory diagram in the case of gripping the mucous membrane in the lesion portion or its adjacent portion by using a grip clamp projected from the first channel for inserting the treatment tool according to the first embodiment.

FIGS. 1 to 7 relate to the first embodiment of the present invention. FIG. 1 is a front view of an edge portion of an endoscope inserting portion in an endoscope apparatus. FIG. 2 is a cross-sectional view of the edge side of the endoscope inserting portion in the longitudinal direction. FIG. 3 is a perspective view showing, of first and second treatment-tool oscillating bases, the second treatment-tool oscillating base. FIG. 4 is an explanatory diagram showing the motion of the second treatment-tool oscillating base and, of first and second treatment-tools, a second treatment-tool. FIG. 5 is a first explanatory diagram showing a relationship between a field of view and the first and second treatment-tools. FIG. 6 is a second explanatory diagram showing a relationship between the field of view and the first and second treatment-tools. FIG. 7 is an explanatory diagram in the case of excising the mucous membrane in the lesion portion or its adjacent portion by using the first and second treatment-tools.

An endoscope inserting portion 1 shown in FIGS. 1 and 2 connects, from the edge side, an edge portion 2, a bending portion 3 (only that on the edge side shown), and a flexible portion (not shown), serving as a soft member as a whole. A base end portion of the flexible portion is connected to an endoscope operating portion.

Referring to FIG. 1, an edge surface 4 of the edge portion 2 has an observing window 11, two illuminating windows 12 and 13, an air and water feed nozzle 14, a front water-feed port 15, and two treatment-tool oscillating bases (first treatment-tool oscillating base 31 and second treatment-tool oscillating base 41).

The observing window 11 has an observation optical system 21. The illuminating windows 12 and 13 have illumination optical systems 22 and 23. The front water-feed port 15 can feed water in the observing direction.

An image pick-up device (not shown) is arranged backward of the observation optical system 21.

In the back of the illumination optical systems 22 and 23, a light guide fiber (not shown) for guiding illumination light to the illuminating windows 12 and 13 is arranged.

The air and water feed nozzle 14 is opened toward the center direction of the outer surface of the observing window 11 in the observation optical system 21, is a water feed nozzle which sprays a cleaning solution to the outer surface of the observing window 11 so as to clean the lens surface, and is an air feed nozzle which feeds air to the observing window 11 and the living body.

The first treatment-tool oscillating base 31 is remotely operated by a first operating wire 32. The first treatment-tool oscillating base 31 is oscillated substantially in the vertical direction of the endoscope image which is observed by an operator.

The second treatment-tool oscillating base 41 is remotely operated by two operating wires of a second operating wire 42 and a third operating wire 43. The second treatment-tool oscillating base 41 is oscillated substantially in the horizontal direction of the endoscope image.

A direction P shown in FIG. 1 is substantially in the upper direction of the endoscope image. A treatment tool inserting portion 48 is formed to the second treatment-tool oscillating base 41, as will be described later.

An electrical insulating cover 16 covers the outer surface of the edge portion 2. The electrical insulating cover 16 has opening portions 17 and 18 which are formed by opening, at the necessary and minimum level, portions at which the first treatment-tool oscillating base 31 and the second treatment-tool oscillating base 41 are arranged.

A cross-sectional position in the cross sectional view of the endoscope inserting portion shown in FIG. 2 corresponds to an A-A' line shown in FIG. 1.

Referring to FIG. 2, the edge portion 2 has an edge constructing portion 10 which is made of metal as the internal structure. The bending portion 3 is arranged to the rear end side of the edge portion 2. The bending portion 3 has a bending tube 6 having a plurality of bending pieces 5 (only one on the front end side is shown). The outer peripheral portion of the bending tube 6 is covered with a bending rubber 7 made of fluorine rubber.

A string 8 is wound to an end portion of the bending rubber 7, and the bending rubber 7 is watertightly fixed by pressing and putting the bending rubber 7 in the inner peripheral direction to touch it to the edge constructing portion 10.

In the back of the first treatment-tool oscillating base 31 and the second treatment-tool oscillating base 41, a first channel opening portion 35 in a first channel 34 for inserting the treatment tool and a second channel opening portion 45 in a second channel 44 for inserting the treatment tool are opened.

A hand end side of the first channel 34 for inserting the treatment tool and a hand end side of the second channel 44 for inserting the treatment tool are opened to the outer surface of the endoscope operating portion (not shown).

The first treatment-tool oscillating base 31 and the second treatment-tool oscillating base 41 are rotatably attached to the edge constructing portion 10 by a first rotating shaft 36 and a second rotating shaft 46.

A solid line of the first treatment-tool oscillating base 31 shows a complete inverted state and a two-dotted line of the first treatment-tool oscillating base 31 shows a maximum stand-up state.

A first treatment tool 37 projected from the first treatment-tool oscillating base 31 is guided to the outside of a field of view from the inside thereof of the endoscope image, or to the inside of the field of view from the outside, substantially in the vertical direction. That is, the first treatment-tool oscillating base 31 guides a first treatment tool 37 guided via the first channel 34 for inserting the treatment tool in a first reciprocating direction.

The second treatment-tool oscillating base 41 guides a second treatment tool 47 substantially in the horizontal direction (front and back directions of the sheet) in the field of view of the endoscope image. That is, the second treatment-tool oscillating base 41 guides the second treatment tool 47 guided via the second channel 44 for inserting the treatment tool in a second reciprocating direction different from the guiding direction of the first treatment tool 37.

Base end portions of the first operating wire 32, the second operating wire 42 (refer to FIG. 1), and the third operating wire 43 (refer to FIG. 1) for remotely operating the first treatment-tool oscillating base 31 and the second treatment-tool oscillating base 41 are connected to a mechanism for operating the treatment-tool oscillating base in the endoscope operating portion via the endoscope inserting portion 1.

The second rotating shaft 46 is inserted from the outer peripheral direction of the edge constructing portion 10, and the electrical insulating cover 16 limits a pull-out direction of the second rotating shaft 46.

The projecting amount L from the edge surface upon moving the edge of the first treatment tool 37 out of the field of view is approximately 10 mm or more for easy observation and treatment.

FIG. 3 is an appearance view showing the second treatment-tool oscillating base 41.

Referring to FIG. 3, the second treatment-tool oscillating base 41 contains a disc-shaped metal. The second treatment-tool oscillating base 41 has a treatment tool inserting portion 48 which is bored through the diameter direction of the disc.

A rotating shaft hole 49 into which the second rotating shaft 46 shown in FIG. 2 is inserted is formed in the center of the second treatment-tool oscillating base 41. Notch portions 53 and 54 are formed near the right side of an upper surface 51 and near the left side of a lower surface 52 in the second treatment-tool oscillating base 41. Further, opened hole portions 55 and 56 in which the second operating wire 42 and the third operating wire 43 are inserted are formed to the second treatment-tool oscillating base 41.

The second operating wire 42 and the third operating wire 43 are rotatably attached to the opened hole portions 55 and 56 in the back direction thereof via wire end members 57 and 58.

The second treatment-tool oscillating base 41 may be ported by one rotating shaft shown in FIG. 3 or may be ported by two rotating shafts.

The second treatment-tool oscillating base 41 is slid to the edge constructing portion 10 by the two surfaces of the upper surfaces 51 and 52, and the material thereof is not limited.

Next, a description is given of the second treatment-tool oscillating base 41 and the projected second treatment tool 47 with reference to FIG. 4.

Referring to FIG. 4, the second operating wire 42 and the third operating wire 43 are stretched, thereby rotating second treatment-tool oscillating base 41 in the horizontal direction with the second rotating shaft 46 as center.

The rotation is limited by projecting an A surface of the edge constructing portion 10 to a rear end surface B of the second treatment-tool oscillating base 41. Maximum stroke lengths of the second operating wire 42 and the third operating wire 43 as the two rotation limitations are set to be shorter than that of a stretching stopper structure (not shown) arranged in a guide-base operating mechanism (not shown), not in the edge portion 2 shown in FIG. 4.

When the second treatment-tool oscillating base 41 is neutral (the second treatment tool 47 is straight), tension is applied to the second operating wire 42 and the third operating wire 43. Then, the second operating wire 42 and the third operating wire 43 are connected to a mechanism for operating the treatment-tool oscillating base (not shown) on the hand side.

The treatment tool inserting portion 0.48 has an opening portion 501 on the front end side narrower than an opening portion 502 on the rear end side.

The opening portion 501 on the front end side is narrower than the second channel opening portion 45.

The opening portion 502 on the rear end side is wider than the second channel opening portion 45.

The second treatment tool 47 projected from the second treatment-tool oscillating base 41 moves substantially in the horizontal direction within a range 59 which is not over the field of view of the endoscope image (observing range) as shown by the solid line and a broken line in FIG. 4.

Although the edge of the second treatment tool 47 is arcuately moved, it may straightly be moved.

A description is given of the motion of the first treatment tool 37 projected from the first treatment-tool oscillating base 31 and the second treatment tool 47 projected from the second treatment-tool oscillating base 41, by operating the guiding bases with reference to FIGS. 5 and 6.

Referring to FIGS. 5 and 6, the inside of a frame 60 is within the field of view of an endoscope image 61 which is observed by an operator, and the outside of the frame 60 is out of the field of the endoscope image 61.

As shown in FIGS. 5 and 6, the screen size of the endoscope image 61 has a length in the horizontal direction longer than that in the vertical direction.

In a state shown in FIG. 5, the edge of the first treatment tool 37 is moved substantially in the vertical direction of the field of view (inside of the frame 60) of the endoscope image 61, and can be guided from the inside of the field of view in the endoscope image 61 to the outside of the field of view, and on the other hand, from the outside of the field of view to the inside.

The edge of the second treatment tool 47 moves substantially in the horizontal direction of the field of view of the endoscope image 61, and does not move out of the field of view.

In a state shown in FIG. 6, a part of the hand side (hatched portion) of the first treatment tool 37 is viewed in the field of the endoscope image 61. However, the edge of the first treatment tool 37 is out of the field of view.

Referring to FIGS. 5 and 6, an arrow F shows water fed from the front water-feed port 15 within the field of view. The water from the front water-feed port 15 fed substantially toward a center S1 of the field of view. The edge locus of the second treatment tool 47 may not be substantially straight but may be curved.

Hereinbelow, a using method of the endoscope apparatus will be described according to the first embodiment.

Referring to FIG. 7, the endoscope inserting portion 1 with the above structure is inserted in the living body.

Next, a chemical such as physiological saline is injected to the lower layer of a lesion mucous membrane 62 by using a needle disposable, and a mucous membrane 63 including the lesion mucous membrane 62 rises.

Next, as shown by a dotted line in FIG. 7, the lesion mucous membrane 62 or its adjacent portion is gripped by a grip clamp 71 as a first treatment-tool projected from the first channel 34 for inserting the treatment tool.

As shown by a solid line in FIG. 7, the grip clamp 71 stands up by the first treatment-tool oscillating base 31, and the mucous membrane 63 including the lesion mucous membrane 62 is picked up.

In this case, the edge of the grip clamp 71 is guided out of the field of view (out of the observing range).

An incision tool 72 as a second treatment-tool projected from the second channel 44 for inserting the treatment tool is remotely operated by the second treatment-tool oscillating base 41. The picked-up mucous membrane 63 or the lower layer thereof is incised in the horizontal direction. In this case, if the incision tool 72 moves fully in the horizontal direction, it is always viewed within the field of view.

According to the first embodiment, since the grip clamp 71 as the first treatment-tool is guided out of the field of view, the grip clamp 71 does not become an obstacle of the incision operation upon incising the mucous membrane 62 including the lesion mucous membrane 63 by the incision tool 72 as the second treatment-tool. Thus, the treatment tools are projected from the edge openings of at least two channels for inserting the treatment tool, and the operability is improved in the treatment using the endoscope.

Further, the lesion portion is easily observed.

In addition, since the incision tool 72 is always viewed within the field of view in the entire range guided, the accurate incision is performed within the field of view.

Since the second operating wire 42 and the third operating wire 43 are always stretched straightly from the neutral state to the rotating state of the second treatment-tool oscillating base 41, the second treatment tool 47 is guided with high response in the horizontal direction.

Further, the rotating limitation of the second treatment-tool oscillating base 41 is set to the edge portion 2 and the guide-base operating mechanism (not shown) and the maximum stroke length of the operating wire of the edge portion 2 is shorter. Therefore, if the second treatment tool 47 is a hard treatment tool with a thick diameter, the length of the second treatment-tool 47 is set to have the amount in consideration of the stretch amount of the operating wire in the halfway, and the amount of rotation determined by the rotating limitation of the edge portion 2 is transmitted without fail.

Further, a size relationship of the opening portion 501 on the front end side, the opening portion 502 on the rear end side, and the second channel opening portion 45 is (opening portion 501 on the front end side<second channel opening portion 45<opening portion 502 on the rear end side). Thus, the second treatment tool 47 is easily inserted in the second treatment-tool oscillating base 41. In this case, since the opening portion 501 on the front end side is the narrowest, the shaking amount of treatment tools is reduced upon guiding and the accurate incision is performed.

Further, since the screen size of the endoscope image has a side in the horizontal direction longer than that in the vertical direction, the guiding range of the second treatment tool 47 (incision tool 72) is widened and the first treatment tool 37 (grip clamp 71) is easily guided to the outside of the field of view.

Conventionally, the above operation is performed by placing the treatment tools out of field of view. However, according to the first embodiment, the above operation is unnecessary and therefore the entire time for treatment operation is reduced.

As mentioned above, the two treatment tools are projected from the edge openings of the two channels for inserting the treatment tool and are guided by the first and second treatment-tool oscillating bases. In the case of the treatment using the endoscope for the lesion portion with the two treatment tools, one treatment-tool is moved out of field of view of the endoscope image as necessity. Consequently, the inconvenience that the two treatment tools are always viewed in the narrow screen is solved. In addition to the above inconvenience, the treatment tools are not touched upon actual treatment and the operation using the grip clamp and the incision tool is smooth and accurate.

Figure 8:
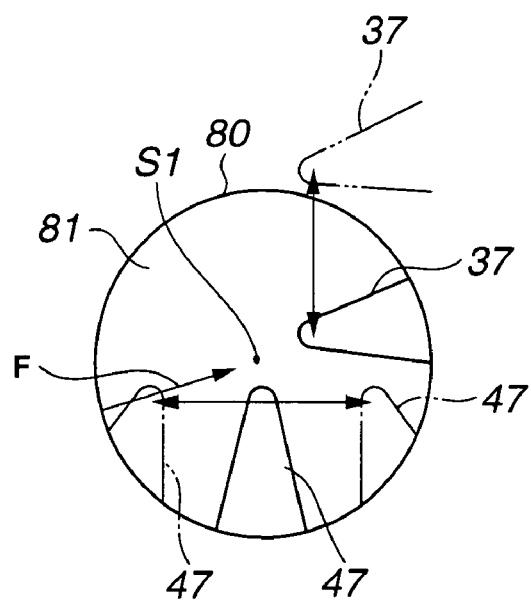
FIG. 8 is a second explanatory diagram showing a relationship between a circular field of view and the first and second treatment-tools according to a modification of the first embodiment.

FIG. 8 is a second explanatory diagram showing a relationship between the circular field of view and the first and second treatment-tools according to a modification of the fist embodiment shown in FIGS. 1 to 7.

Referring to FIG. 8, when an endoscope image 81 observed by the operator has a circular field-of-view 80, only the shape of the field of view is different from that shown in FIG. 5. The motions of the first treatment tool 37 and the second treatment tool 47 are the same.

Water from the front water-feed port 15 shown by the arrow F is fed substantially toward the center S1 of the circular field-of-view 80.

Second Embodiment

Figure 9:
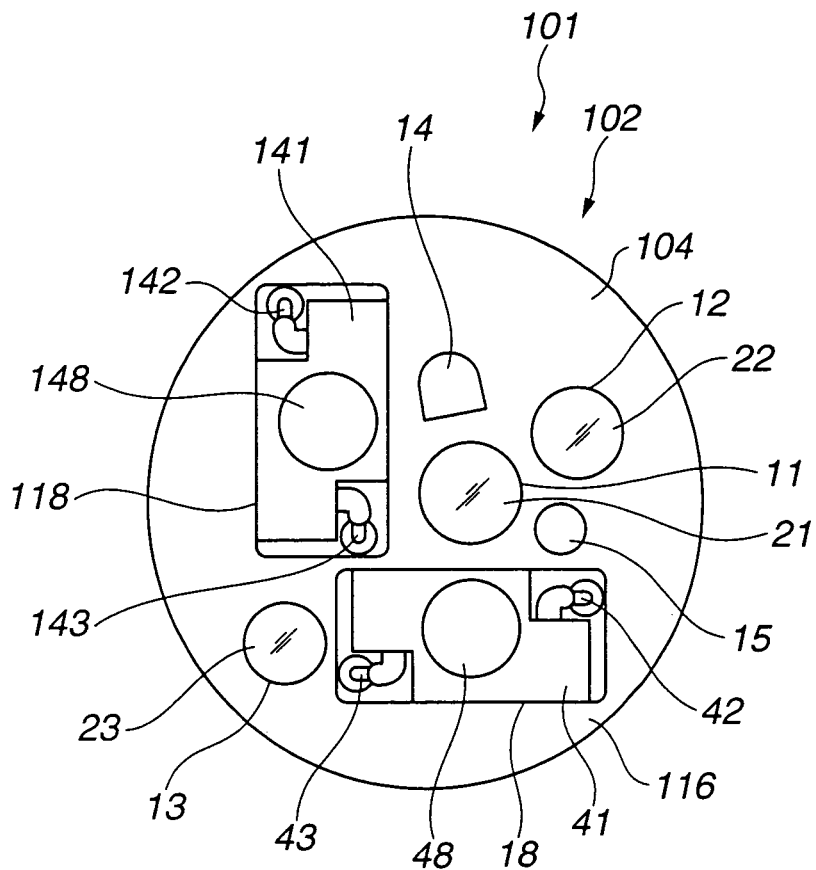
FIG. 9 is a front view showing an edge portion of an endoscope inserting portion according to a second embodiment of the present invention.
Figure 10:
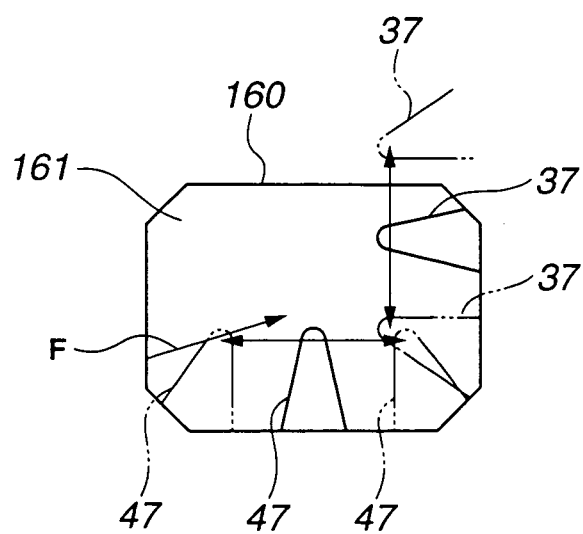
FIG. 10 is an explanatory diagram showing a relationship between the field of view and first and second treatment-tools according to the second embodiment.

FIGS. 9 and 10 relate to the second embodiment of the present invention. FIG. 9 is a front view showing an edge portion of an endoscope inserting portion. FIG. 10 is an explanatory diagram showing a relationship between a field of view and first and second treatment-tools.

According to the second embodiment, referring to FIGS. 9 and 10, the same components as those shown in FIGS. 1 to 7 according to the first embodiment are designated by the same reference numerals and a description thereof is omitted here.

Referring to FIG. 9, an edge surface 104 of an edge portion 102 in an endoscope inserting portion 101 includes the observing window 11, the two illuminating windows 12 and 13, the air and water feed nozzle 14, the front water-feed port 15, and two treatment-tool oscillating bases (a first treatment-tool oscillating base 141 and the second treatment-tool oscillating base 41). The second treatment-tool oscillating base 41 is the same as that according to the first embodiment.

The first treatment-tool oscillating base 141 has an attaching position and an attaching angle different from those of the second treatment-tool oscillating base 41. However, the other structure of the first treatment-tool oscillating base 141 is the same as that of the second treatment-tool oscillating base 41.

The outer surface of the edge portion 102 is covered with an electrical insulating cover 116. The electrical insulating cover 116 has opening portions 117 and 18 which are formed by opening, at the necessary and minimum level, portions at which the first treatment-tool oscillating base 141 and the second treatment-tool oscillating base 41 are arranged.

The first treatment-tool oscillating base 141 is remotely operated by two operating wire 142 and operating wire 143. The first treatment-tool oscillating base 141 is oscillated substantially in the vertical direction of the endoscope image. The first treatment-tool oscillating base 141 has a treatment tool inserting portion 148 forming an inserting hole.

Referring to FIG. 10, the edge of the first treatment tool 37 is guided from the inside of field of view of an endoscope screen 161 (the inside of a frame 160) to the outside thereof, or from the outside of field of view to the inside, substantially in the vertical direction.

The edge of the second treatment tool 47 is guided substantially in the horizontal direction within the filed of view of the endoscope screen 161.

According to the second embodiment, the same advantages as those according to the first embodiment are obtained. Since the first treatment-tool oscillating base 141 is operated by the two operating wires 142 and 143, the treatment tool guided to the first treatment-tool oscillating base 141 is guided with high response without fail not only in one direction but also in two directions. Further, since the treatment tool guided to the first treatment-tool oscillating base 141 is guided to a wide range, the treatment property is improved as compared with that according to the first embodiment.

Third Embodiment

Figure 11:
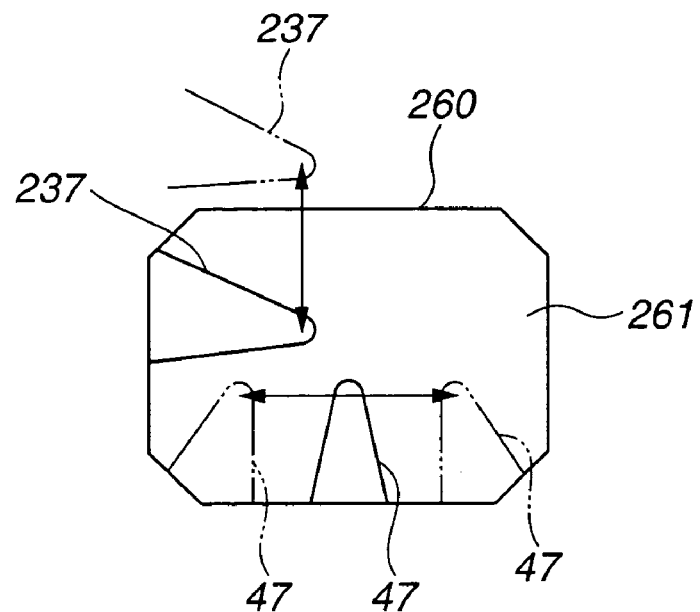
FIG. 11 is an explanatory diagram showing a relationship between the field of view and first and second treatment-tools according to a third embodiment of the present invention.

FIG. 11 is an explanatory diagram showing a relationship between the field of view and first and second treatment-tools according to the third embodiment of the present invention.

According to the third embodiment, referring to FIG. 11, the same components as those shown in FIGS. 1 to 7 according to the first embodiment are designated by the same reference numerals and a description thereof is omitted here.

Referring to FIG. 11, an edge of a first treatment tool 237 moves on the left of a field of view (in a frame 260) of an endoscope screen 261 substantially in the vertical direction, is guided from the inside of field of view to the outside of field of view, on the other hand, from the outside of field of view to the inside of field of view.

The edge of the second treatment tool 47 moves within the field of view of the endoscope screen 261 substantially in the horizontal direction, and does not exceed the inside of the field of view.

Although not shown, positions of the first channel 34 for inserting the treatment tool and the first treatment-tool oscillating base 31 to the observing window 11 shown in FIG. 1 are contrary to those according to the first embodiment on the right and left, in the endoscope apparatus according to the third embodiment.

According to the third embodiment, only the guiding position of the first treatment tool 237 is contrary to that of the first treatment tool 37 according to the first embodiment on the right and left. Other operations are the same as those according to the first embodiment.

According to the third embodiment, the same advantages as those according to the first embodiment are obtained.

Fourth Embodiment

Figure 12:
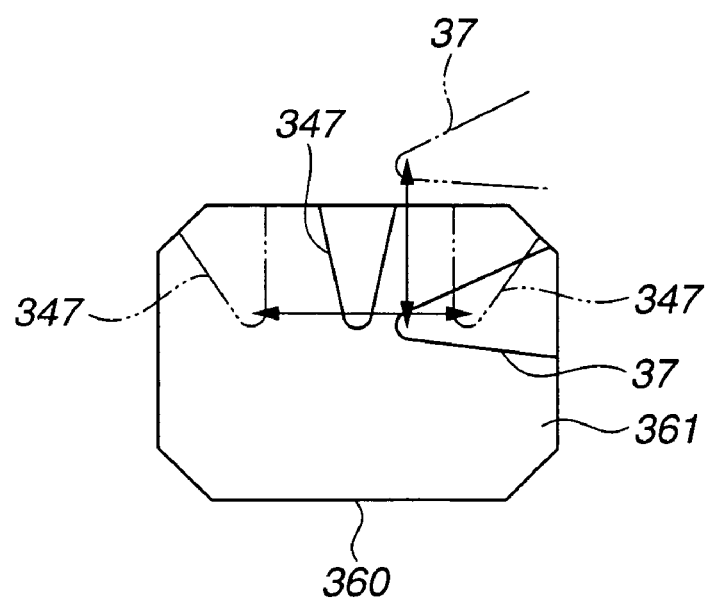
FIG. 12 is an explanatory diagram showing a relationship between the field of view and first and second treatment-tools according to a fourth embodiment of the present invention.

FIG. 12 is an explanatory diagram showing a relationship between the field of view and first and second treatment-tools according to the fourth embodiment of the present invention.

According to the fourth embodiment, referring to FIG. 12, the same components as those shown in FIGS. 1 to 7 according to the first embodiment are designated by the same reference numerals and a description thereof is omitted here.

Referring to FIG. 12, an edge of a second treatment tool 347 moves substantially on the right and left on the top side of a field of view of an endoscope screen 361 (in a frame 360), and does not exceed the inside of the field of view.

In the endoscope apparatus according to the fourth embodiment, the positions of the second channel 44 for inserting the treatment tool and the second treatment-tool oscillating base 41 to the observing window 11 shown in FIG. 1 are contrary to those of the fist embodiment on the top and bottom.

According to the fourth embodiment, only the guiding position of the second treatment tool 347 is contrary to that of the second treatment tool 47 shown in FIG. 5 according to the first embodiment on the top and bottom. Other operations are the same as those according to the first embodiment.

According to the fourth embodiment, the same advantages as those according to the first embodiment are obtained.

Fifth Embodiment

Figure 13:
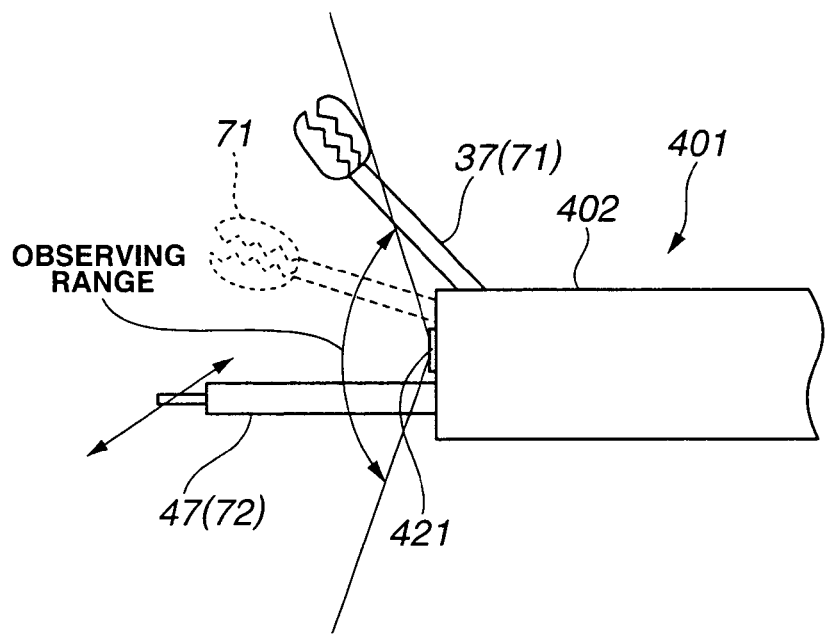
FIG. 13 is a side view showing an edge portion of an endoscope inserting portion according to a fifth embodiment of the present invention.
Figure 14:
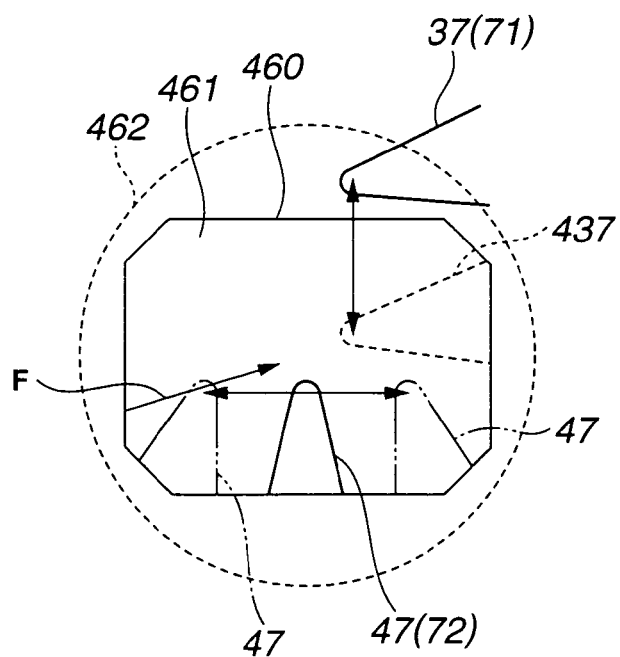
FIG. 14 is an explanatory diagram showing a relationship between the field of view and first and second treatment-tools according to a fifth embodiment of the present invention.

FIGS. 13 and 14 relate to the fifth embodiment of the present invention. FIG. 13 is a side view showing an edge portion of an endoscope inserting portion. FIG. 14 is an explanatory diagram showing a relationship between the field of view and first and second treatment-tools.

According to the fifth embodiment, referring to FIG. 13, the same components as those shown in FIGS. 1 to 7 according to the first embodiment are designated by the same reference numerals and a description thereof is omitted here.

Referring to FIG. 13, an observation optical system 421 arranged to an edge portion 402 of an endoscope inserting portion 401 has an angle wider than that of the observation optical system 21 according to the first embodiment, and the grip clamp 71 projected from the first channel for inserting the treatment tool is viewed within a field-of-view range 462 (refer to FIG. 14) of the observation optical system 421 in the maximum stand-up state.

However, according to the fifth embodiment, the edge of the grip clamp 71 as the first treatment tool is limited by imaging processing such as masking of the field of view of the endoscope image so that the edge of the grip clamp 71 comes, to the outside of field of view of the endoscope image to be observed by the operator, from the inside.

Referring to FIG. 14, a frame 462 indicates a range of the field of view of the observation optical system 421, and a frame 460 indicates a range of the field of view of an endoscope image 461 on a monitor to be observed by the operator. According to the fifth embodiment, the field of view is limited by the masking of display means such as the monitor, thereby moving, out of the field of view of the endoscope image 461 to be observed by the operator, the edge of the grip clamp 71 in the maximum stand-up state to be viewed by the observation optical system 421.

According to the fifth embodiment, the same advantages as those according to the first embodiment are obtained.

According to the first to fifth embodiments, as shown in FIGS. 1 to 5, the image pick-up device which transmits the optical image formed by the observation optical system to the base end side of the endoscope inserting portion as electrical means is used as optical image transmitting means for transmitting the optical image to the base end side of the endoscope inserting portion by the optical or electrical means. The optical image transmitting means may be used to transmit the optical image to the base end side of the endoscope inserting portion as the endoscope image including a fiber scope and optical means. That is, the present invention can be applied to both an optical endoscope including the fiber scope and an electrical endoscope including a video scope.

According to the first to fifth embodiments, as shown in FIGS. 1 to 14, only the edge portion of the first treatment-tool of the first and second treatment-tools is adjusted to come to the outside of field of view of the endoscope image to be observed by the operator from the inside. However, only the edge portion of the second treatment-tool of the first and second treatment-tools is adjusted to come to the outside of field of view of the endoscope image to be observed by the operator from the inside. Further, both the first and second treatment-tools may be adjusted to come to the outside of field of view of the endoscope image to be observed by the operator from the inside.

Sixth Embodiment

Figure 15:
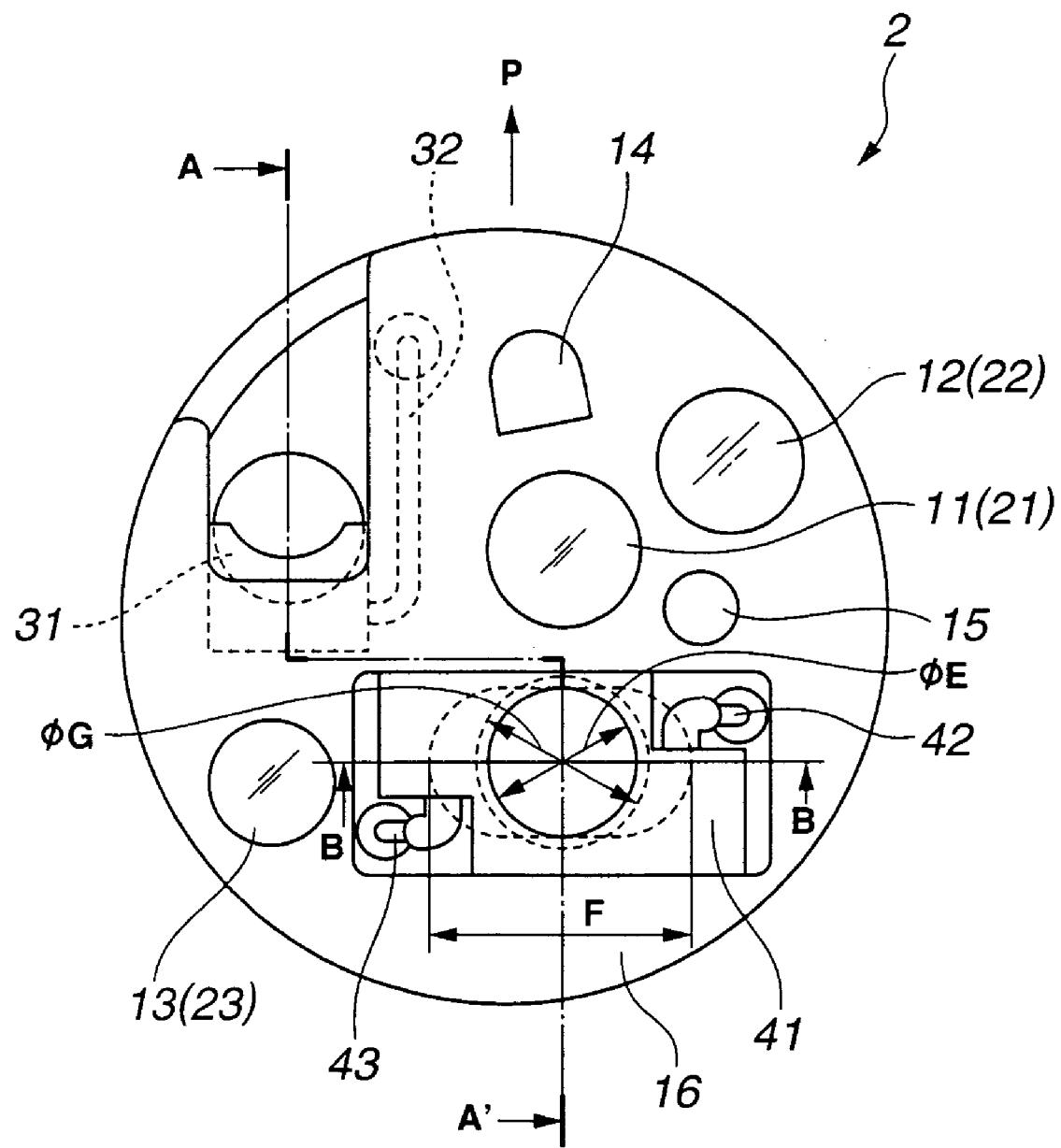
FIG. 15 is a front view showing the structure of an edge portion of an endoscope inserting portion in an endoscope apparatus according to a sixth embodiment of the present invention.
Figure 16:
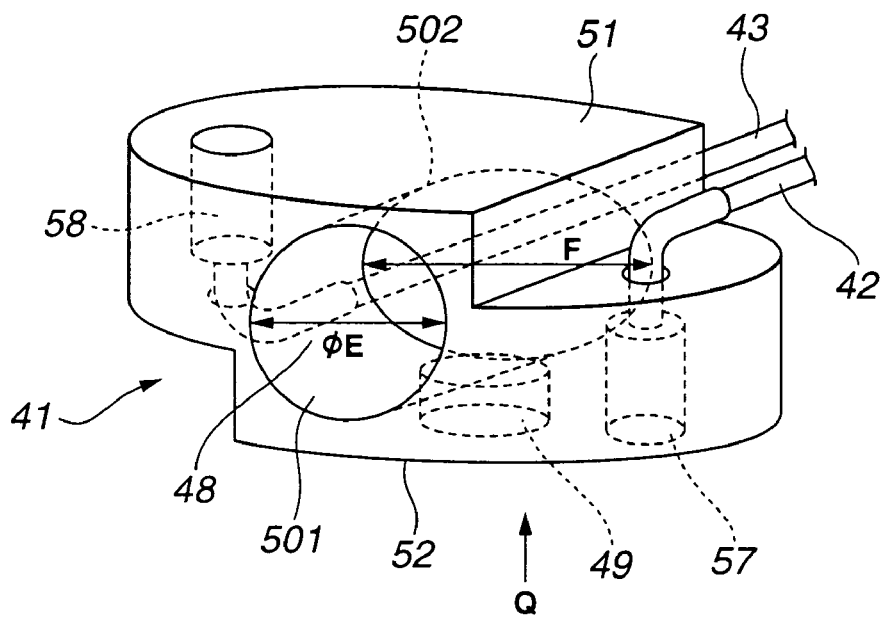
FIG. 16 is a perspective view showing, of first and second treatment-tool oscillating bases, the second treatment-tool oscillating base in the endoscope apparatus according to the sixth embodiment.
Figure 17:
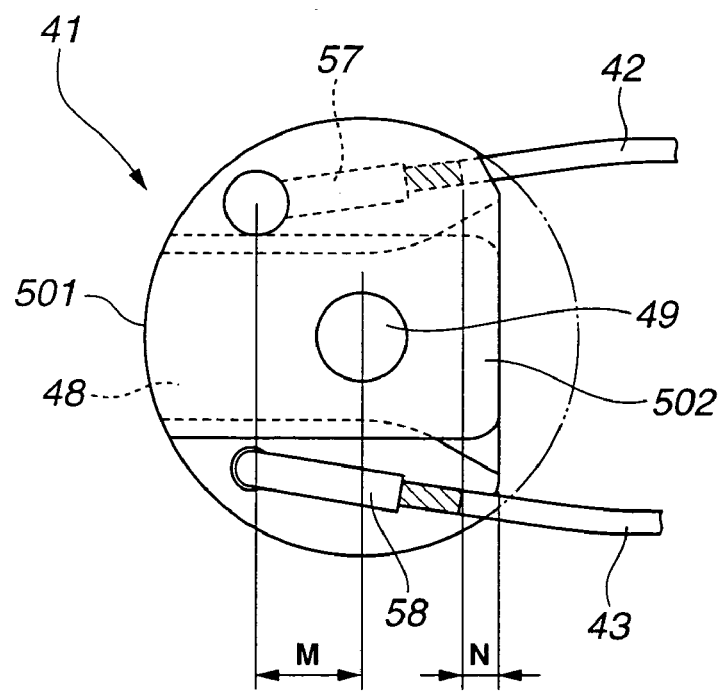
FIG. 17 is a bottom view showing the second treatment-tool oscillating base in the endoscope apparatus according to the sixth embodiment.
Figure 18:
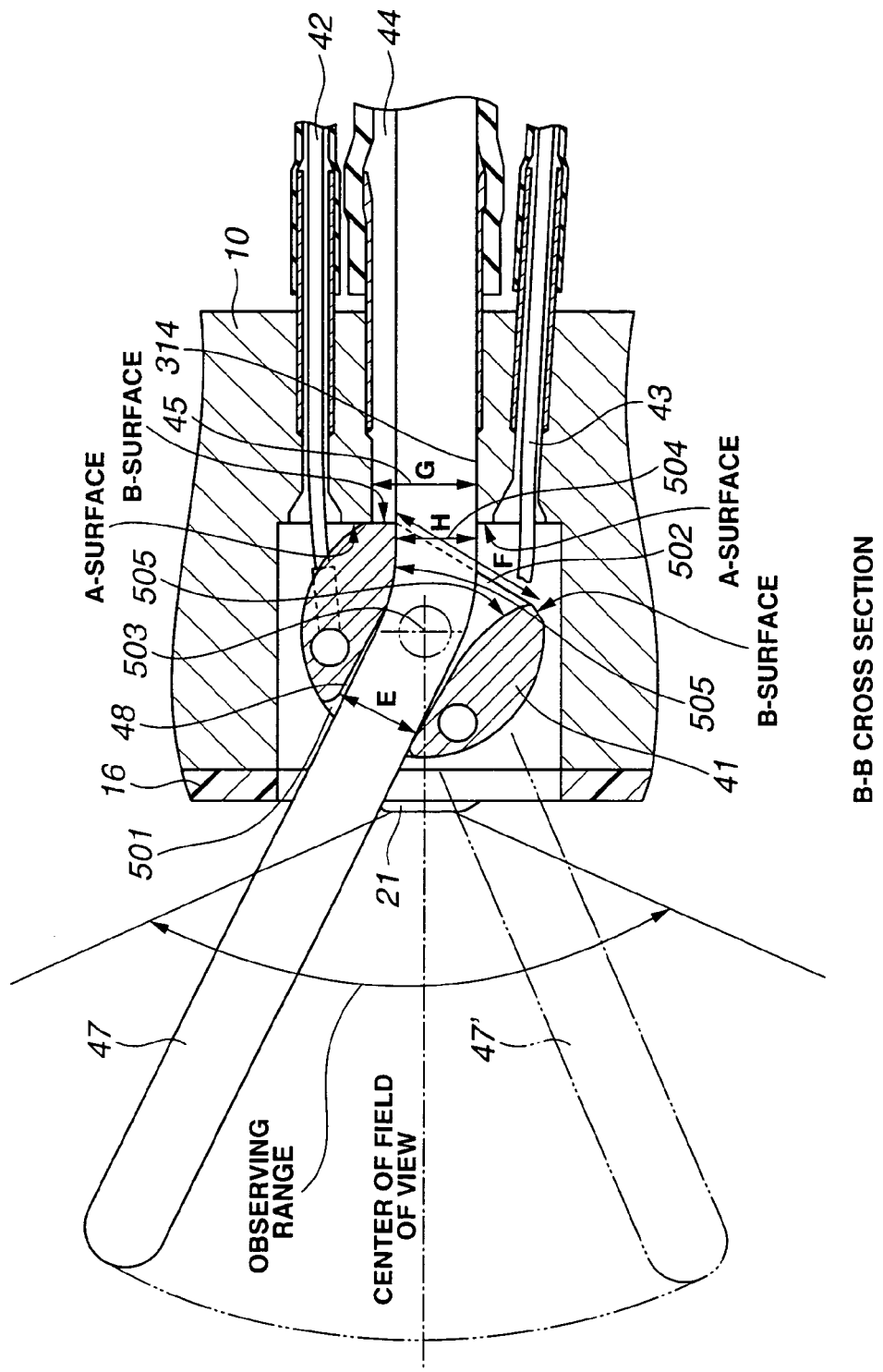
FIG. 18 is a cross-sectional view showing the structure of the second treatment-tool oscillating base arranged to the edge portion of the endoscope inserting portion in the endoscope apparatus according to the sixth embodiment.

FIGS. 15 to 18 relate to the sixth embodiment of the present invention. FIG. 15 is a front view showing the structure of an edge portion of an endoscope inserting portion in an endoscope apparatus. FIG. 16 is a perspective view showing a second treatment-tool oscillating base in the endoscope apparatus. FIG. 17 is a bottom view showing the second treatment-tool oscillating base in the endoscope apparatus. FIG. 18 is a cross-sectional view showing the structure of the second treatment-tool oscillating base arranged to the edge portion of the endoscope inserting portion in the endoscope apparatus. The same components as those according to the first embodiment shown in FIGS. 1 to 7 are designated by the same reference numerals.

Although not shown, an endoscope apparatus of the present invention comprises an elongated inserting portion which is inserted in the living body and an operating portion arranged to the base end of the inserting portion. The endoscope inserting portion connects, from the edge side, an edge portion, a bending portion, and a flexible portion. A base end portion of the flexible portion is connected to the operating portion. The operating portion comprises a bending mechanism for bending the bending portion, a hole for inserting the treatment tool, a mechanism for standing up the treatment tool, and a universal cord including a light guide or a signal cable.

Referring to FIG. 15, the edge portion 2 of the endoscope inserting portion in the endoscope apparatus has the observing window 11 in the center of the front surface of the edge portion 2. The observing window 11 has the observation optical system 21 having the objective lens and the solid image pick-up device for converting an observed portion image from the objective lens into an image pick-up signal.

The two illuminating windows 12 and 13 are arranged at the oblique position in FIG. 15, sandwiching the observing window 11. The illuminating windows 12 and 13 have the illumination optical system 22 comprising an illuminating lens and a light guide fiber for guiding illumination light.

The edge portion 2 comprises the air and water feed nozzle 14 which sprays a cleaning solution to the observing window 11 and feeds air to the objective lens and the living body, the front water-feed port 15 which feeds water in the observing direction, the first treatment-tool oscillating base 31, and the second treatment-tool oscillating base 41.

The first treatment-tool oscillating base 31 is arranged on the left of the observing window 11 in FIG. 15, and is remotely operated from an operating portion (not shown) by the first operating wire 32, and the first treatment-tool oscillating base 31 is oscillated substantially in the vertical direction of the endoscope image to be observed by the operator. The second treatment-tool oscillating base 41 is arranged in the bottom of the observing window 11 in FIG. 15, two operating wires of the second operating wire 42 and the third operating wire 43 remotely operate the second treatment-tool oscillating base 41, and the second treatment-tool oscillating base 41 is oscillated in substantially in the horizontal direction of the endoscope image.

The direction shown by the arrow P shown in FIG. 1 is a substantially upper direction of the endoscope image. That is, the direction of the arrow P is an upper direction of the screen of the endoscope image displayed on a play and display monitor based on the image pick-up signal of the observed portion which is picked up and is generated by the solid image pick-up device forming the observation optical system 21 of the observing window 11.

The first treatment-tool oscillating base 31 has an opening portion which is opened from the front surface to the side surface of the edge portion 2. The second treatment-tool oscillating base 41 has an opening portion which is opened only on the front surface of the edge portion 2. The opening portion of the second treatment-tool oscillating base 41 may be opened from the front surface to the side surface of the edge portion 2, similarly to the opening portion of the first treatment-tool oscillating base 31.

Referring to FIG. 15, the illuminating window 12 is arranged on the right of the intermediate point between the observing window 11 and the air and water feed nozzle 14. The illuminating window 13 is arranged in the oblique lower direction between the first treatment-tool oscillating base 31 and the second treatment-tool oscillating base 41. The front water-feed port 15 is arranged substantially on the right between the observing window 11 and the second treatment-tool oscillating base 41.

The electrical insulating cover 16 covers the edge portion 2 of the endoscope inserting portion. The covered edge portion 2 has an opened portion at the necessary and minimum level, having the arrangement of the observing window 11, the illuminating windows 12 and 13, the air and water feed nozzle 14, the front water-feed port 15, the first treatment-tool oscillating base 31, and second treatment-tool oscillating base 41.

The first treatment-tool oscillating base 31 shown in FIG. 15 is in a completely inverted state, and the second treatment-tool oscillating base 41 is in a state in which the treatment tool in the neutral state is straightly projected from the treatment-tool oscillating base.

The internal structure of the first treatment-tool oscillating base 31 and the second treatment-tool oscillating base 41 in the edge portion 2 are the same as that shown in FIG. 2 according to the first embodiment. That is, an A-A' line cross-sectional view in FIG. 15 is similar to that shown in FIG. 2.

The edge of the first operating wire 32 is connected to the first treatment-tool oscillating base 31, and the edges of the second operating wire 42 (not shown in FIG. 15) and the third operating wire 43 are connected and are fixed to the second treatment-tool oscillating base 41. Base ends of the first operating wire 32, the second operating wire 42, and the third operating wire 43 are connected to the mechanism for operating the treatment-tool oscillating base which is inserted in the inserting portion and which is arranged to the operating portion, thereby remotely being operated by the mechanism for operating the treatment-tool oscillating base.

Next, a description is given of the appearance structure of the second treatment-tool oscillating base 41 with reference to FIG. 16. The second treatment-tool oscillating base 41 is cylindrical as a whole, which is formed by partly cutting an arcuate portion on the hand side. The treatment tool inserting portion 48 is formed by inserting a second treatment tool 47 in the diameter direction from the side surface whose arcuate portion is cut. The center portion of the lower surface 52 of the second treatment-tool oscillating base 41 has a second rotating shaft hole 49 in which the second rotating shaft 46 is inserted.

The upper surface 51 and the lower surface 52 of the second treatment-tool oscillating base 41 have notch surfaces arranged in different directions. Edges of the second operating wire 42 and the 43 are rotatably attached to the notch surfaces via wire end members 57 and 58.

That is, the second operating wire 42 and the third operating wire 43 are operated, thereby being rotated in the horizontal direction with the first rotating shaft hole 49 as center. The second treatment-tool oscillating base 41 may be rotated by a single operating wire as well as the two operating wires (the second operating wire 42 and the third operating wire 43).

The two surfaces of the upper surface 51 and the lower surface 52 of the second treatment-tool oscillating base 41 are slid with the edge constructing portion 10 as sliding surfaces, and the area of the upper surface 51 is the same as that of the lower surface 52. A material forming the second treatment-tool oscillating base 41 is not limited but, preferably, is a metallic material such as stainless steel or electric insulating member such as ceramics.

As mentioned above, the second treatment tool 47 is inserted in the treatment tool inserting portion 48 arranged to the second treatment-tool oscillating base 41. The shape of an opening portion 501 on the front end side of the treatment tool inserting portion 48 is substantially circular, and the shape of an opening portion 502 on the rear end side is substantially oval. A smooth continuous surface is formed between the opening portion 501 on the front end side and the opening portion 502 on the rear end side and the entire shape is substantially funnel-shaped.

A description is given of a relationship between the second operating wire 42 and the third operating wire 43 which are arranged to the second treatment-tool oscillating base 41 with reference to FIG. 17. FIG. 17 is a bottom view showing the second treatment-tool oscillating base 41 viewed in the direction of an arrow Q shown in FIG. 16.

Terminals of the second operating wire 42 and the third operating wire 43 attached to the second treatment-tool oscillating base 41 are attached to wire end members 57 and 58. The wire end members 57 and 58 are arranged at the position on the edge side of the second rotating shaft hole 49 by a distance M.

The ends of the second operating wire 42 and the third operating wire 43 are attached to the wire end members 57 and 58 by soldering or silver waxing. A seeping length (hatched portion in the drawing) of the soldering or silver waxing which is seeped to the ends of the second operating wire 42 and the third operating wire 43 soldered or silver-waxed to the wire end members 57 and 58 is equal to a distance N to the second rotating shaft hole 49 from an end surface having the opening portion 502 on the rear end side in the longitudinal direction of the treatment tool inserting portion 48 in the second treatment-tool oscillating base 41.

A description is given of the structure for attaching the second treatment-tool oscillating base 41 with the above-mentioned structure to the edge portion 2 with reference to FIG. 18. FIG. 18 is a cross-sectional view showing the structure of the second treatment-tool oscillating base 41 cut from a B-B cut-off line shown in FIG. 15 viewed in an arrow direction.

The second treatment-tool oscillating base 41 is arranged near the edge side of the second channel opening portion 45 in the second channel 44 for inserting the treatment tool, and is rotatably attached by the second rotating shaft 46. The end portions of the second operating wire 42 and the third operating wire 43 are attached by the wire end member 57 and the wire end member 58.

The second operating wire 42 and the third operating wire 43 are stretched, thereby oscillating the second treatment-tool oscillating base 41 in the horizontal direction with a center 503 of the second rotating shaft 46 as center. The center 503 of the second rotating shaft 46 substantially matches the center of field of view.

The second treatment-tool oscillating base 41 is subjected to the horizontal rotating limitation by projecting an A surface of the edge constructing portion 10 to a B surface on the rear end side which is formed by cutting the arcuate portion of the second treatment-tool oscillating base 41. That is, the second channel opening portion 45 is sandwiched and thus the second treatment-tool oscillating base 41 is subjected to the rotating limitation by the edge constructing portion 10 at both sides of the openings.

If the second treatment-tool oscillating base 41 is in the neutral state (the treatment tool 47 to which the treatment tool inserting portion 48 of the second treatment-tool oscillating base 41 is inserted is straight), the second operating wire 42 and the third operating wire 43 are stretched by tension. The guide-base operating mechanism of the operating portion (not shown) remotely operates the second operating wire 42 and the third operating wire 43.

A width E (diameter) of the opening portion 501 on the front end side of the treatment tool inserting portion 48 in the second treatment-tool oscillating base 41 is narrower than a width F (long diameter of the oval) of the opening portion 502 on the rear end side in the treatment tool inserting portion 48 (E<F). The width F of the opening portion 502 on the rear end side in the treatment tool inserting portion 48 is wider than a width G (diameter) of the second channel opening portion 45 (F>G). That is, a relationship among the width G of the second channel opening portion 45 and the widths E and F of the opening portion 501 on the front end side and the opening portion 502 on the rear end side in the treatment tool inserting portion 48 is (E<G<F).

The second treatment tool 47 inserted from the second treatment-tool inserting hole in the operation portion is inserted in the second channel 44 for inserting the treatment tool, and is projected to the front-outside of the edge surface 4 of the edge portion 2 via the second channel opening portion 45, the opening portion 502 on the rear end side of the treatment tool inserting portion 48 in the second treatment-tool oscillating base 41, and the opening portion 501 on the front end side of the treatment tool inserting portion 48 in the second treatment-tool oscillating base 41.

Referring to FIG. 18, the second treatment tool 47 is oscillated and is guided in the horizontal direction by the second treatment-tool oscillating base 41 within the range of field of view of the observing range.

The second treatment tool 47 shown by a solid line in FIG. 18 shows a state in which it is maximally oscillated and guided on the left of the endoscope image read and displayed based on the image pick-up signal that is picked up and is generated by the observation optical system 21. A second treatment tool 47' indicated by a two-dotted line in FIG. 18 is maximally oscillated and guided on the right of the endoscope image.

When the second treatment-tool oscillating base 41 is maximally oscillated and guided on the left, a width H of a substantial opening portion 504 is formed by the opening portion 502 on the rear end side of the second treatment-tool oscillating base 41 and the second channel opening portion

45. The width H is equal to or more than the width E of the opening portion 501 on the front end side in the treatment tool inserting portion 48 (H≧E). The minimum inserting width of the treatment tool inserting portion 48 is equal to the width E of the opening portion 501 on the front end side in the treatment tool inserting portion 48.

In other words, when the second treatment-tool oscillating base 41 is maximally oscillated and guided, a side surface 505 of the treatment tool inserting portion 48 continuously arranged to the opening portion 501 on the front end side from the opening portion 502 on the rear end side is substantially in parallel with a side surface 514 of the opening portion in the second channel opening portion 45.

That is, the side surface 505 of the inserting portion from the opening portion 502 on the rear end side of the treatment tool inserting portion 48 when the second treatment-tool oscillating base 41 is maximally oscillated and guided is substantially in parallel with the side surface 514 of the opening portion of the second channel opening portion 45. As a consequence, the second treatment tool 47 is inserted to the second channel opening portion 45 from the second channel 44 for inserting the treatment tool, and the advancing and returning insertion is possible in the longitudinal direction without the sandwiching of the base portion of the second treatment tool 47 which is inserted and is projected to the opening portion 501 on the front end side from the opening portion 502 on the rear end side of the treatment tool inserting portion 48 in the second treatment-tool oscillating base 41. Upon exchanging the second treatment tool 47, the insertion is easy because the side surface 314 of the opening portion of the second channel opening portion 45 is substantially in parallel with the side surface 505 of the inserting portion of the opening portion 502 on the rear end side in the second treatment-tool oscillating base 41 when the second treatment-tool oscillating base 41 is maximally oscillated and guided.

According to the sixth embodiment, the edge portion of the endoscope inserting portion has the treatment-tool oscillating bases near the opening portion of the channel for inserting the treatment tool. If the treatment tool is maximally oscillated and driven by the treatment-tool oscillating bases, the advancing and returning insertion is easy in the longitudinal direction of the treatment tool without the treatment tool being caught. Further, the edge portion with the small size is formed without fail so as to easily exchange the treatment tool.

Seventh Embodiment

Figure 19:
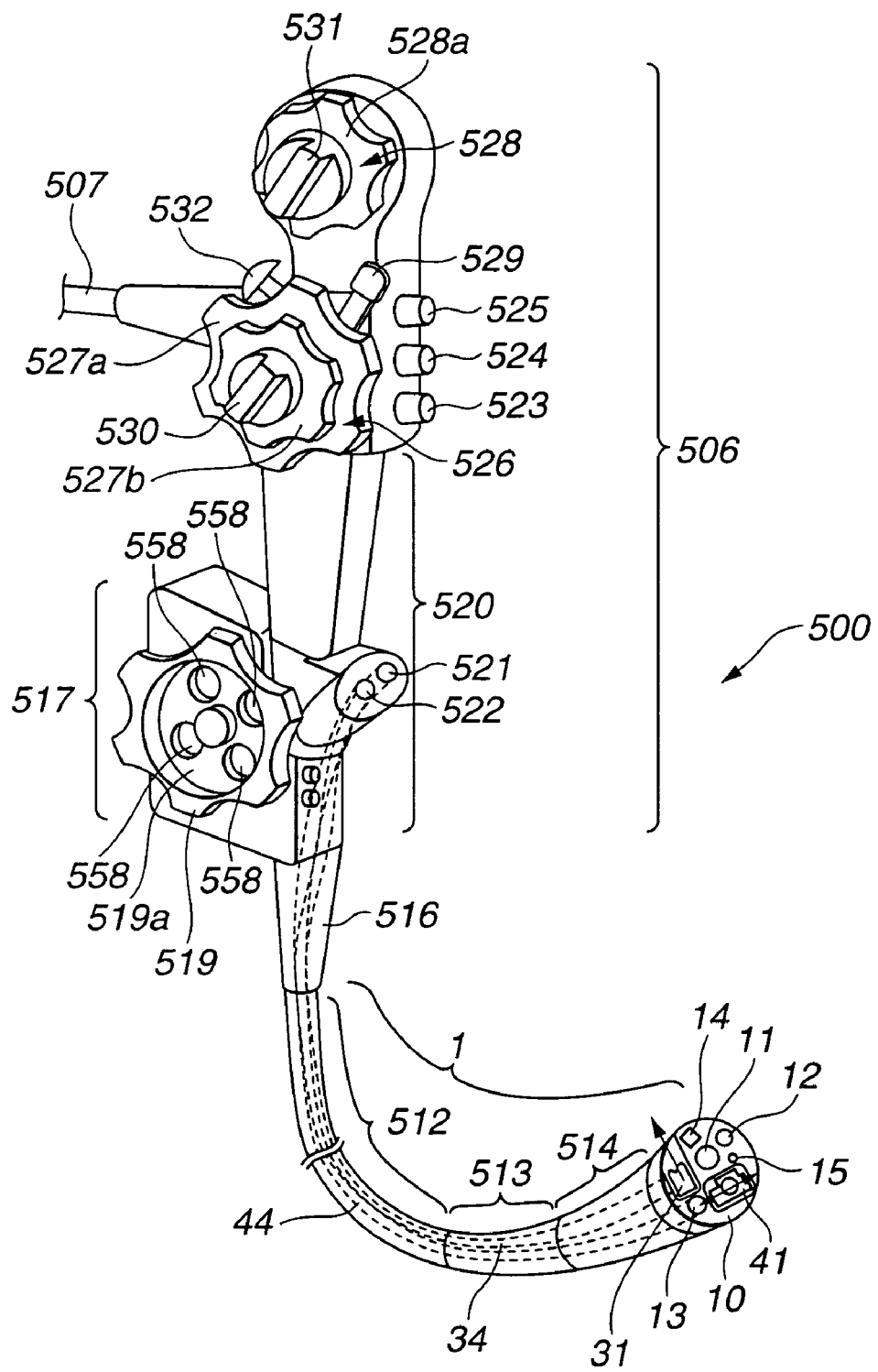
FIG. 19 is a perspective view showing the entire structure of an endoscope apparatus according to a seventh embodiment of the present invention.
Figure 20:
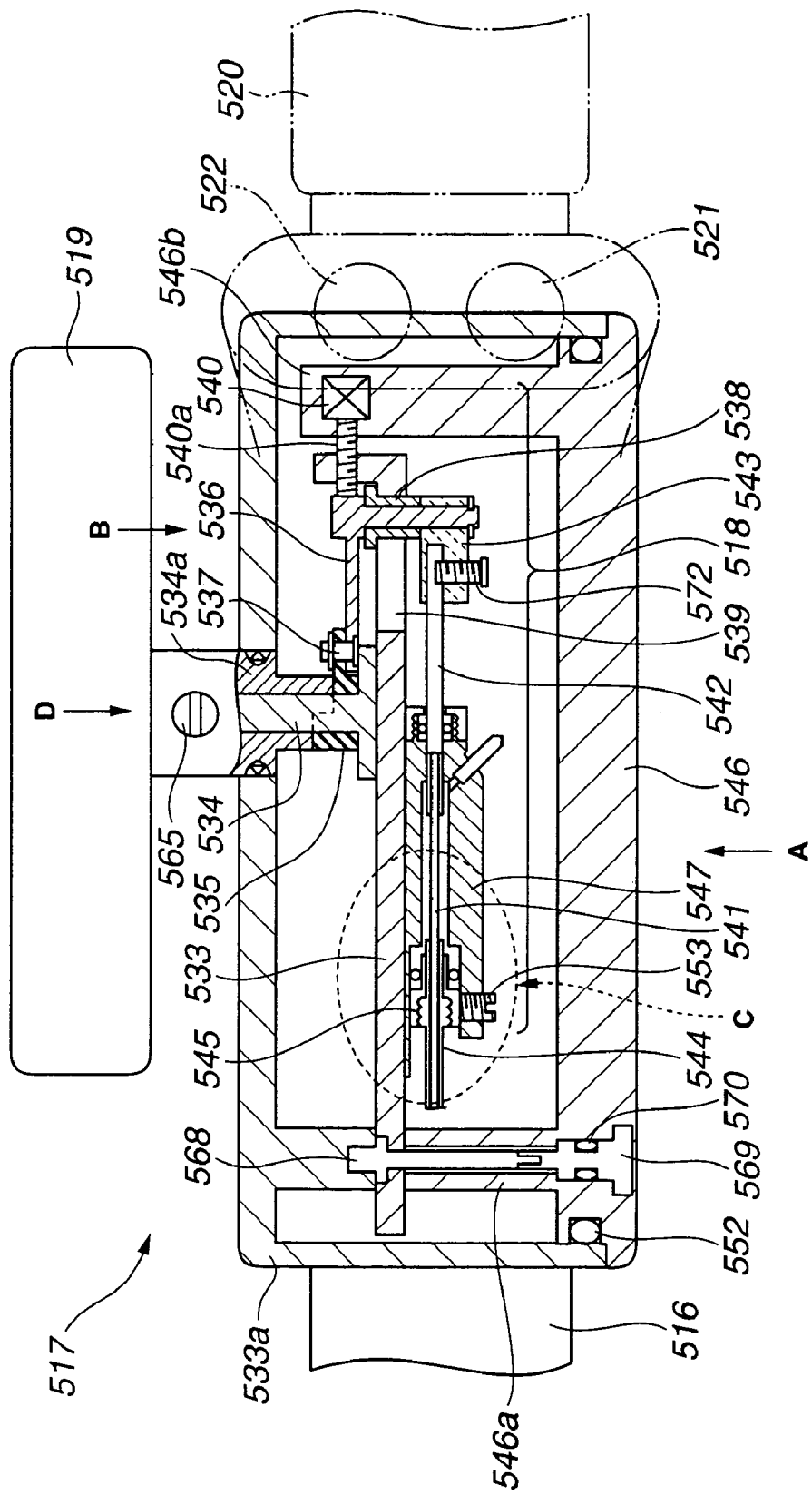
FIG. 20 is a cross-sectional view showing the structure of an oscillating-base operating portion in the endoscope apparatus according to the seventh embodiment.
Figure 21:
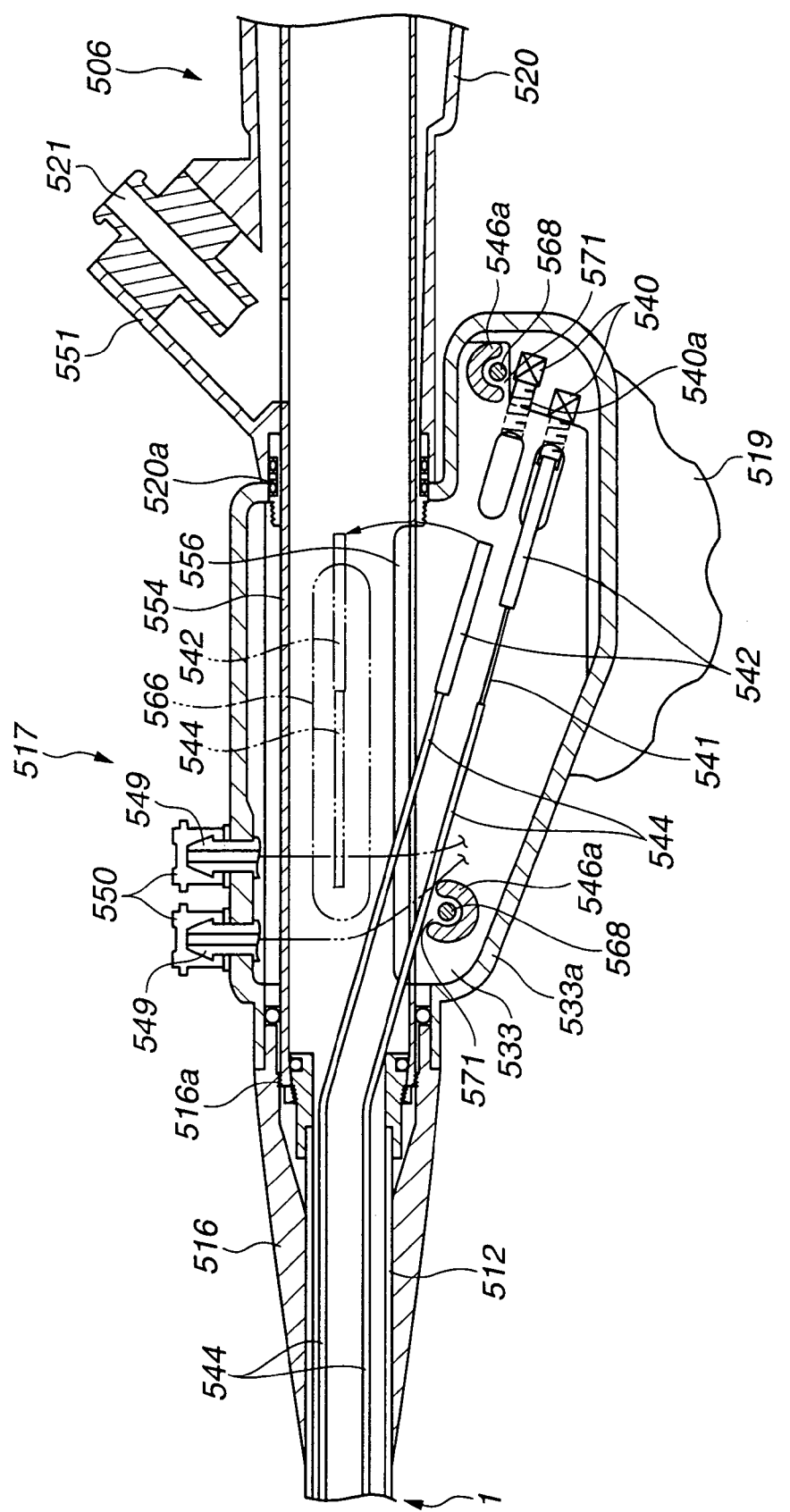
FIG. 21 is a cross-sectional view in the case of removing component parts from the oscillating-base operating portion in the endoscope apparatus viewed from an arrow A shown in FIG. 20.

FIGS. 19 to 21 relate to the seventh embodiment. FIG. 19 is a perspective view showing the entire structure of an endoscope apparatus. FIG. 20 is a cross-sectional view showing the structure of an oscillating base operating portion in the endoscope apparatus. FIG. 21 is a cross-sectional view in the case of cutting a part from the oscillating base operating portion in the endoscope apparatus viewed from an arrow A shown in FIG. 20.

A description is given of the entire structure of the endoscope apparatus according to the seventh embodiment of the present invention referring to FIG. 19. An endoscope apparatus 500 of the present invention comprises the endoscope inserting portion 1 and an operating portion 506.

The endoscope inserting portion 1 is formed of, from the edge side, the edge constructing portion 10, a first bending portion 514, a second bending portion 513, a flexible portion 512, and a bending preventing portion 516, and the entire shape of the endoscope inserting portion 1 is elongated.

The operating portion 506 sequentially comprises an oscillating base operating portion 517, a grip portion 520, a first bending knob portion 526, and a second bending knob portion 528, from the side for connecting the base end of the bending preventing portion 516 in the endoscope inserting portion 1.

A universal code 507 including a light guide fiber is connected to the operating portion 506.

The edge constructing portion 10 of the endoscope inserting portion 1 has the observing window 11, the illuminating window 12, the air and water feed nozzle 14, the front water-feed port 15, the first treatment-tool oscillating base 31, and the second treatment-tool oscillating base 41.

The observing window 11 has an objective lens and a solid image pick-up device. An image pick-up signal of the observed portion is transmitted to an image signal processing device (not shown) via the endoscope inserting portion 1, the operating portion 506, and a signal cable arranged to the universal code 507, and an image pick-up screen is displayed on a monitor based on a video signal generated by the image signal processing device.

An illuminating lens is arranged to the illuminating windows 12 and 13, projects illumination light guided by the light guide fiber included in the universal code 507, the operating portion 506, and the endoscope inserting portion 1. The observed portion is thus illuminated through the illuminating lens.

Water and air is fed to the air and water feed nozzle 14 by operating a button 523 for controlling the feed of air and water, which will be described later, arranged to the operating portion 506. The front water-feed port 15 is connected to a front water-feed cap (not shown) arranged to a connector (not shown) at one end of the universal code 507, and the water is fed by a syringe or a water feed pump from the front water feed cap.

The second treatment-tool oscillating base 41 is oscillated in the horizontal direction in the drawing by a first oscillating base operating knob 519 of an oscillating base operating portion 517, which will be described later. The first treatment-tool oscillating base 31 is oscillated in the vertical direction in the drawing by a first oscillating base operating knob 532 arranged to a first bending knob portion 526, which will be described later.

Openings are arranged in front of the first treatment-tool oscillating base 31 and the second treatment-tool oscillating base 41, the treatment tools are projected from the edge constructing portion 10, and they are oscillated in the horizontal and vertical directions by the first treatment-tool oscillating base 31 and second treatment-tool oscillating base 41.

The first bending portion 514 of the endoscope inserting portion 1 is bent in four directions of right, left, upper, and lower directions by the first bending knob portion 526 in the operating portion 506. The second bending portion 513 is bent in two directions upper and lower, or right and left directions by a second bending knob portion 528 in the operating portion 506.

The first treatment-tool oscillating base 31 and the second treatment-tool oscillating base 41 in the edge constructing portion 10 comprise a first hole 521 for inserting the treatment tool arranged to a grip portion 520 of the operating portion 506, and the second channel 44 for inserting the treatment tool and the first channel 34 for inserting the treatment tool included in the endoscope inserting portion 1 from the second hole 522 for inserting the treatment tool. That is, the treatment tools inserted from the first hole 521 for inserting the treatment tool and the second hole 522 for inserting the treatment tool are inserted to the first treatment-tool oscillating base 31 and the second treatment-tool oscillating base 41 via the first channel 34 for inserting the treatment tool and the second channel 44 for inserting the treatment tool.

The bending preventing portion 516 of the endoscope inserting portion 1 prevents the bending at the portion for connecting the base end of the flexible portion 512 and the oscillating base operating portion 517 of the grip portion 520. Thus, referring to FIG. 21, the bending preventing portion 516 is screwed to a cylindrical structure 554 of the operating portion arranged in the grip portion 520 by a screw portion 516a.

The first oscillating base operating knob 519 is arranged to the oscillating base operating portion 517 of the operating portion 506. Further, the oscillating base operating portion 517 of the operating portion 506 includes an operating mechanism 518 for the first treatment-tool oscillating base (refer to FIG. 20) for oscillating the second treatment-tool oscillating base 41 by the first oscillating base operating knob 519, which will be described later. A caved portion 519a is arranged to the first oscillating base operating knob 519, and a plurality of openings 558 are arranged to the caved portion 519a. The openings 558 are provided so as not to be accumulated with a cleaning solution, an antiseptic solution, and a rinse agent at the first oscillating base operating knob 519 upon cleaning and sterilizing the endoscope apparatus 500.

As mentioned above, a first hole 521 for inserting the treatment tool and a second hole 522 for inserting the treatment tool are arranged to the front surface side of the grip portion 520 in the operating portion 506. The first hole 521 for inserting the treatment tool is placed on the opposite side of the setting side of the first oscillating base operating knob 519, and is arranged on the left viewed from the operator. The second hole 522 for inserting the treatment tool is placed on the setting side of the first oscillating base operating knob 519, and is arranged on the right viewed from the operator. The treatment tool inserted from the second hole 522 for inserting the treatment tool is inserted in the first channel 34 for inserting the treatment tool and the treatment tool is arranged on the right side from the operator upon projecting the treatment tool from the first treatment-tool oscillating base 31. Thus, the erroneous recognition and the confused operation of the treatment tool are prevented.

In front of the first bending knob portion 526 and the second bending knob portion 528 and on the top of the grip portion 520, a button 523 for controlling the feed of air and water, a suction control button 524, and an image recording button 525 are arranged.

The first bending knob portion 526 comprises a vertical-operating knob 527a for the first bending portion which bents the first bending portion 514 of the endoscope inserting portion 1 in the vertical direction, and a horizontal-operating knob 527b for the first bending portion which bents the first bending portion 514 of the opening portion in the horizontal direction.

The vertical-operating knob 527a for the first bending portion and the horizontal-operating knob 527b for the first bending portion are operated, thereby pulling out and returning the bending wire connected to the first bending portion 514 via a bending mechanism (not-shown). Consequently, the first bending portion 514 is bent in the vertical and horizontal directions.

Further, the driving of rotation and the fixing of the vertical-operating knob 527a for the first bending portion are switched by a first vertical-rotating/fixing lever 529. The driving of rotation and the fixing of the horizontal-operating knob 527b for the first bending portion are switched by a first horizontal-rotating/fixing knob 530.

The first bending knob portion 526 has the first oscillating base operating knob 532. The first oscillating base operating knob 532 is operated, thereby oscillating the first treatment-tool oscillating base 31 of the edge constructing portion 10 in the upper direction via the oscillating base operating mechanism.

Further, a second bending knob portion 528 is arranged in the vertical direction of the first bending knob portion 526 of the grip portion 520. The second bending knob portion 528 comprises a second bending knob 528a, and a second rotating/fixing knob 531. The second bending knob portion 528 has a bending mechanism (not shown) for bending the second bending portion 513 of the second bending knob 528a in the horizontal or vertical direction.

That is, the operation of the second bending knob 528a causes the bending wire connected to the second bending portion 513 via the bending mechanism to be pulled out or be returned. Thus, the second bending portion 513 is bent in the vertical or horizontal direction.

The driving of rotation and the fixing of the second bending knob 528a are switched by the second rotating/fixing knob 531.

Next, a description is given of the structure of the oscillating base operating portion 517 in the endoscope apparatus 500 with reference to FIGS. 20 and 21. FIG. 20 is a cross-sectional view showing the structure of the oscillating base operating portion 517 in the endoscope apparatus 500 in view of the first hole 521 for inserting the treatment tool and the second hole 522 for inserting the treatment tool.

A substrate 533 of the operating main body arranged in a frame 533a for operating the oscillating base is fixed by a screw to a cylindrical structure 554 of the operating portion (refer to FIG. 21). The first oscillating base operating knob 519 is arranged to the side surface of the frame 533a for operating the oscillating base, and a cylindrical shaft 534a is arranged in the center of the first oscillating base operating knob 519. A cylindrical shaft 534a pierces through the side surface of the frame 533a for operating the oscillating base, and is inserted to the outer peripheral of a fixing shaft 534 fixed to the substrate 533 of the operating main body-arranged in the frame 533a for operating the oscillating base.

That is, the cylindrical shaft 534a of the first oscillating base operating knob 519 is rotatably fit into the fixing shaft 534 fixed to the substrate 533 of the operating main body of the frame 533a for operating the oscillating base.

A rotating plate 535 is attached and is fixed to the edge of the cylindrical shaft 534a of the first oscillating base operating knob 519. The rotating plate 535 is rotatably fit into the fixing shaft 534. That is, the rotation of the first oscillating base operating knob 519 rotates a rotating plate 535 via the cylindrical shaft 534a.

A pair of brackets 543 is rotatably attached to the edges slid and fit to a guide groove 539 of the pair of L-shaped rods 536 via a lubricating member 538.

The pair of stoppers 540 for adjusting the moving distance or stopping the motion of the rods 536 is attached to a substrate 533 of the operating main body.

The pair of stoppers 540 is formed by screwing a male screw to a substrate 533 of the operating main body in opposite of the straight moving direction of the rods 536. That is, the edges of the stoppers 540 adjust the amount of projection to the rods 536 by a screw pitch 540a of the male screw.

Thus, upon rotating the first oscillating base operating knob 519, the roads 536 can be rotated within a range for abutting the rods 536 to the stoppers 540. The screw pitch 540a is processed with a thin pitch, thereby adjusting the moving range of the roads finely.

A wire connecting member 542 as a part of an operation transmitting member is detachably fixed to the brackets 543 attached to the edge portion of the rods 536 by a screw 572.

A pair of operating wires 541 is extended as a part of the operation transmitting member from the second treatment-tool oscillating base 41. The end portion of the operating wires 541 is fixed and is connected to the wire connecting member 542 by soldering and waxing.

The operating wires 541 are wires having plural twist, and are covered with a tube 544 for guiding the operating wire. The edge side of the tube 544 for guiding the operating wire is fixed to the edge constructing portion 10 of the endoscope inserting portion 1 where the second treatment-tool oscillating base 41 is positioned. The base end side of the tube 544 for guiding the operating wire is screwed to a member 545 for holding the guide tube as shown in FIG. 20, and the member 545 for holding the guide tube is fixed and is held to the edge side of a cylinder 547 by a screw 553, and is watertightly fixed by a watertight member (not shown).

The cylinder 547 is hollow, is attached and is fixed to the substrate 533 of the operating main body. A wire connecting member 542 to which the operating wires 541 are fixed by soldering or waxing is inserted to a hollow portion of the cylinder 547.

The operating mechanism 518 for the first treatment-tool oscillating base comprises a cylindrical shaft 534a of the first oscillating base operating knob 519, the rotating plate 535, the rods 536, the brackets 543, the wire connecting member 542, and the cylinder 547.

In a frame 533a for operating the oscillating base, the operating mechanism 518 for the first treatment-tool oscillating base, the operating wires 541, and the tube 544 for guiding the operating wire are arranged to the substrate 533 of the operating main body. Referring to FIG. 21, the frame 533a for operating the oscillating base is arranged in an outside space from the side surface of the cylindrical structure 554 of the operating portion as a connecting member of the endoscope inserting portion 1 and the operating portion 506.

Therefore, a notch window 556 is arranged to the side surface of the cylindrical structure 554 of the operating portion. The notch window 556 is continuously connected to the frame 533a for operating the oscillating base, and is used for inserting the base end side of the tube 544 for guiding the operating wire in the frame 533a for operating the oscillating base from the endoscope inserting portion 1.

That is, the tube 544 for guiding the operating wire is inserted in the flexible portion 512 from the adjacent portion of the second treatment-tool oscillating base 41 of the endoscope inserting portion 1, is arranged to the cylindrical structure 554 of the operating portion as the connecting member of the endoscope inserting portion 1 and the operating portion 506, and is arranged to the frame 533a for operating the oscillating base from the notch window 556. Further, the tube 544 for guiding the operating wire is attached and is fixed to the member 545 for holding the guide tube arranged to the substrate 533 of the operating main body. Consequently, the operating wires 541 of the second treatment-tool oscillating base 41 is inserted in the tube 544 for guiding the operating wire of the operating portion, and is attached to the wire connecting member 542 by soldering and waxing.

As shown by the two-dotted line in FIG. 21, the cylindrical structure 554 of the operating portion has an assembling opening 566. The assembling opening 566 is arranged to the opposite side of the frame 533a for operating the oscillating base to which the first oscillating base operating knob 519 is arranged.

In the endoscope apparatus of the present invention, the endoscope apparatus 500 comprises the flexible endoscope inserting portion 1 which is inserted in the living body, and the operating portion 506 which is arranged on the hand side of the endoscope inserting portion 1. The endoscope apparatus 500 comprises the bending means (526 and 528) which is arranged to the operating portion 506, bends the bending wire from the bending portion of the endoscope inserting portion 1, and removes and adjusts the loosing of the bending wire; the grip portion 520 which is arranged to the operating portion 506, and is detachable to the bending means (526 and 528), and operates the bending means (526 and 528) by gripping the operating portion 506, the oscillating base operating portion 517 which is arranged to the operating portion 506, is detachable to the endoscope inserting portion 1 side of the grip portion 520, and oscillates the oscillating wire from the treatment-tool oscillating bases (31 and 41) at the endoscope inserting portion 1 arranged apart from the bending means (526 and 528), and the oscillating wire connecting means (543 and 572) which is arranged to the oscillating base operating portion 517, and connects the bending wire from the treatment-tool oscillating bases (31 and 41). Upon loosing the bending wire, after detaching the oscillating wire from the oscillating wire connecting means (543 and 572), the oscillating base operating portion 517 and the grip portion 520 are slid to the endoscope inserting portion 1 and the loosing of the bending wire is removed and is adjusted by the bending means (526 and 528).

The first bending knob portion 526 and the second bending knob portion 528 repeatedly bend the second bending portion 513 and the first bending portion 514 of the endoscope inserting portion 1, thereby loosing the operating wire between the bending portions 513 and 514 and the first and second bending knob portion 526 and 528. A description is given of the sequence for removing and adjusting the loosing of the operating wires.

First, the screwing is reset between the cylindrical structure 554 of the operating portion arranged in the grip portion 520 and the screw portion 516a of the bending preventing portion 516 arranged to the connecting side of the endoscope inserting portion 1 and the operating portion 506. The bending preventing portion 516 is deviated to the flexible portion 512 of the endoscope inserting portion 1.

Next, in order to remove the cover 546 which is attached and is sealed to the opening of the frame 533a for operating the oscillating base, the screwing of a cover supporter stopper 569 to a supporter 568 is reset.

The cover 546 is removed from the frame 533a for operating the oscillating base and, then, the operating mechanism 518 for the first treatment-tool oscillating base, the cylinder 547, and the tube 544 for guiding the operating wire which are arranged in the frame 533a for operating the oscillating base are exposed.

Next, a screw 572 for attaching and fixing the wire connecting member 542 as an operation transmitting member to the brackets 543 forming the operating mechanism 518 for the first treatment-tool oscillating base is detached. Thus, the attachment and fixing of the wire connecting member 542 is reset from the brackets 543.

Next, the screw 553 arranged to the cylinder 547 is detached and the operating wires 541, the wire connecting member 542, the tube 544 for guiding the operating wire, and the member 545 for holding the guide tube, as the operation transmitting members, are detached from the cylinder 547.

As mentioned above, the operating wires 541, the wire connecting member 542, the tube 544 for guiding the operating wire, and the member 545 for holding the guide tube are detached from the cylinder 547. The wire connecting member 542 is detached from the brackets 543. Then, a state shown in FIG. 21 is obtained. FIG. 21 omits the operating mechanism 518 for the first treatment-tool oscillating base and the cylinder 547 in the frame 533*a* for operating the oscillating base of the oscillating base operating portion 517 shown in FIG. 20.

Referring to FIG. 21, the wire connecting member 542 detached from the operating mechanism 518 for the first treatment-tool oscillating base and the cylinder 547 presses the operating wires 541 connected to the end portion to the flexible portion 512 side of the endoscope inserting portion 1 (as shown in FIG. 21, one of the wire connecting member 542 and the operating wires 541 are pressed to the flexible portion 512 side).

The wire connecting member 542 connected to the operating wires 541 pressed to the flexible portion 512 side is pressed in the cylindrical structure 554 of the operating portion from the notch window 556 arranged to the cylindrical structure 554 of the operating portion.

In this case, the wire connecting member 542 connected to the operating wires 541 from the notch window 556 shown in FIG. 21 arranged to the cylindrical structure 554 of the operating portion is pressed, thereby pressing the wire connecting member 542 into the cylindrical structure 554 of the operating portion from the assembling opening 566. Consequently, as shown by a two-dotted line in FIG. 21, the operating wires 541 connected to the wire connecting member 542 is positioned in the cylindrical structure 554 of the operating portion when it is pressed in the tube 544 for guiding the operating wire. That is, the operating wire 541 and the wire connecting member 542 are accommodated in the cylindrical structure 554 of the operating portion while it is fixed by soldering or waxing. The wire connecting member 542 is connected and is fixed to the end portion of the operating wires 541 by soldering or waxing and, in this state, the wire connecting member 542 is pressed in the tube 544 for guiding the operating wire (in the left direction shown in FIG. 21), thereby pressing the operating wires 541 in the tube 544 for guiding the operating wire (relatively in the right direction).

As mentioned above, the wire connecting member 542 of the pair of operating wires 541 for oscillating the second treatment-tool oscillating base 41 is maximally pressed in the cylindrical structure 554 of the operating portion on the flexible portion 512 side and is accommodated in the tube 544 for guiding the operating wire. Then, the screw fixing of the substrate 533 of the operating main body and the cylindrical structure 554 of the operating portion is reset, thereby deviating the frame 533*a* for operating the oscillating base to the flexible portion 512 side of the endoscope inserting portion 1 along the cylindrical structure 554 of the operating portion.

Next, a cap 551 for inserting the treatment tool arranged to the first hole 521 for inserting the treatment tool and the second hole 522 for inserting the treatment tool is detached from the grip portion 520, thereby deviating the grip portion 520 to the flexible portion 512 side in the endoscope inserting portion 1.

As mentioned above, the grip portion 520 is deviated to the endoscope inserting portion 1. Thus, first and second bending mechanisms (not shown) of the first bending knob portion 526 and the second bending knob portion 528 and the bending wires arranged to the first bending portion 514 and the second bending portion 513 are exposed and the loosing of the bending wires is removed and is adjusted. Bending angles of the first bending portion 514 and the second bending portion 513 are set at proper angles.

After ending the removal and adjustment of the loosing of the bending wires, the assembling processing is performed in the way inverse to the foregoing, thereby re-constructing the endoscope apparatus.

In the endoscope apparatus having the bending knob portion for bending the bending portion of the inserting portion arranged to the operating portion and the treatment-tool oscillating base operating portions at the operating portion apart from the knob operating knob, the treatment-tool oscillating base operating portions are deviated to the inserting portion side by resetting the combination of the treatment-tool oscillating base operating mechanism arranged to the treatment-tool oscillating base operating portion and the operating wire arranged between the mechanism for operating the treatment-tool oscillating base and the treatment-tool oscillating base at the inserting portion edge. It is easy to perform the operation for removing and adjusting the losing of the bending wire and the bending mechanism arranged to the operating portion.

Eighth Embodiment

Figure 22:
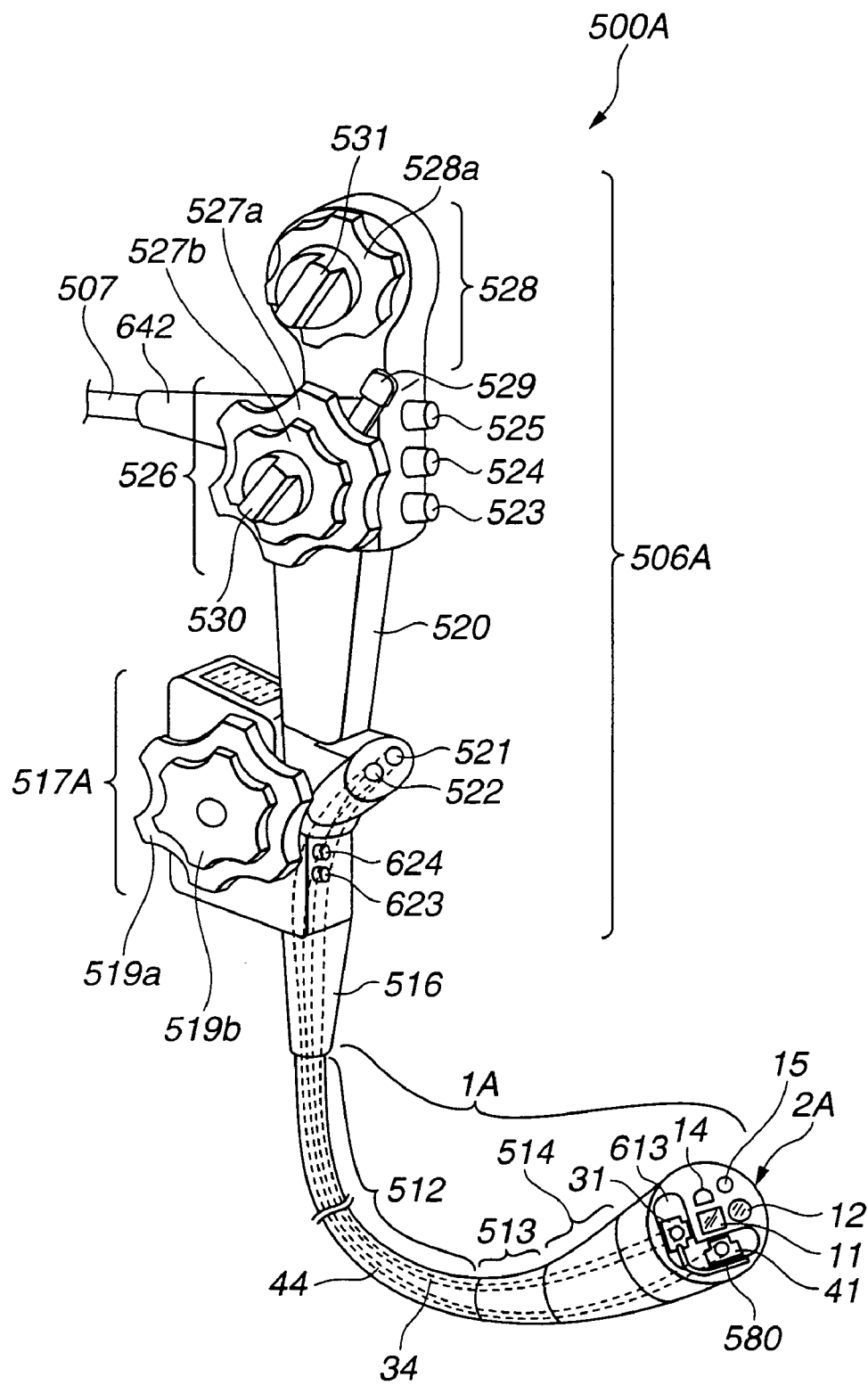
FIG. 22 is a perspective view showing the entire structure of an endoscope apparatus according to an eighth embodiment of the present invention.
Figure 23:
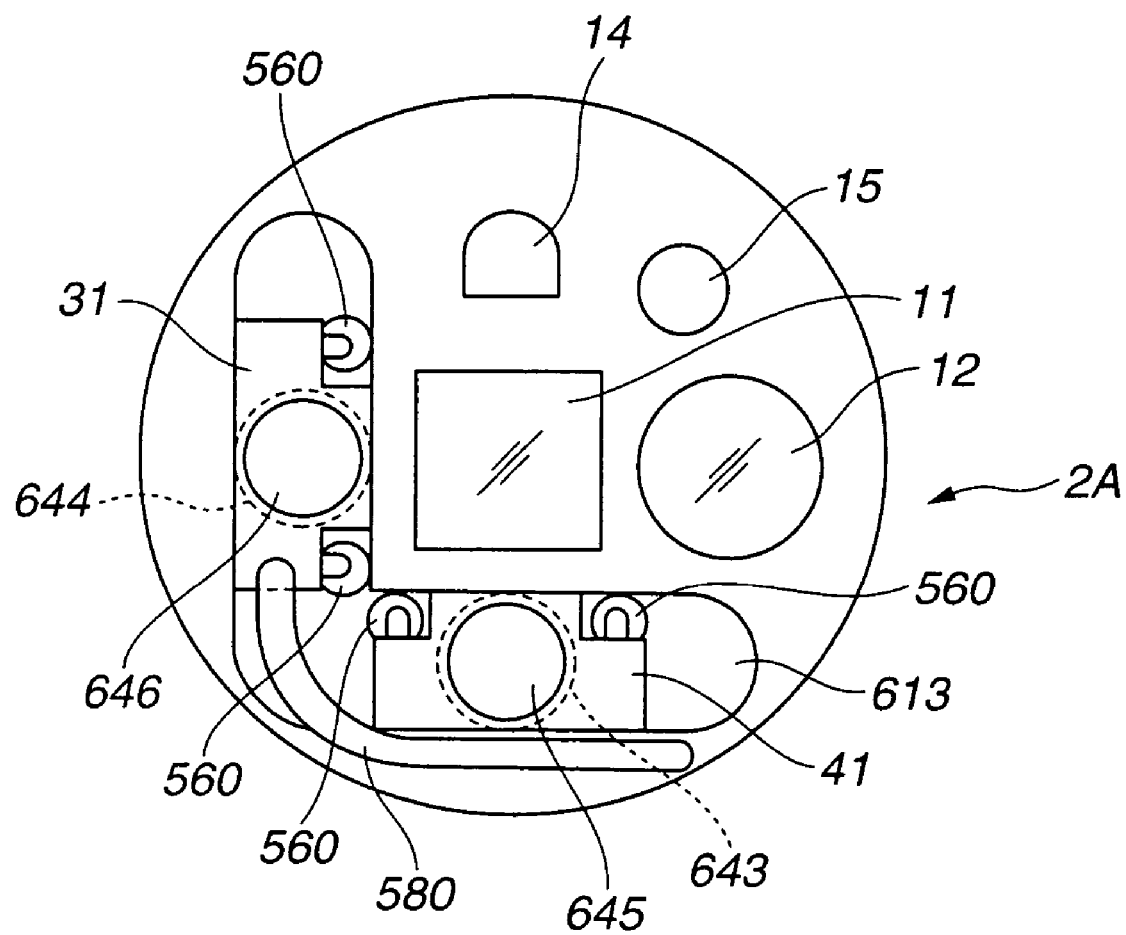
FIG. 23 is a plan view showing an edge portion of an endoscope inserting portion in the endoscope apparatus in front view according to the eighth embodiment.
Figure 24:
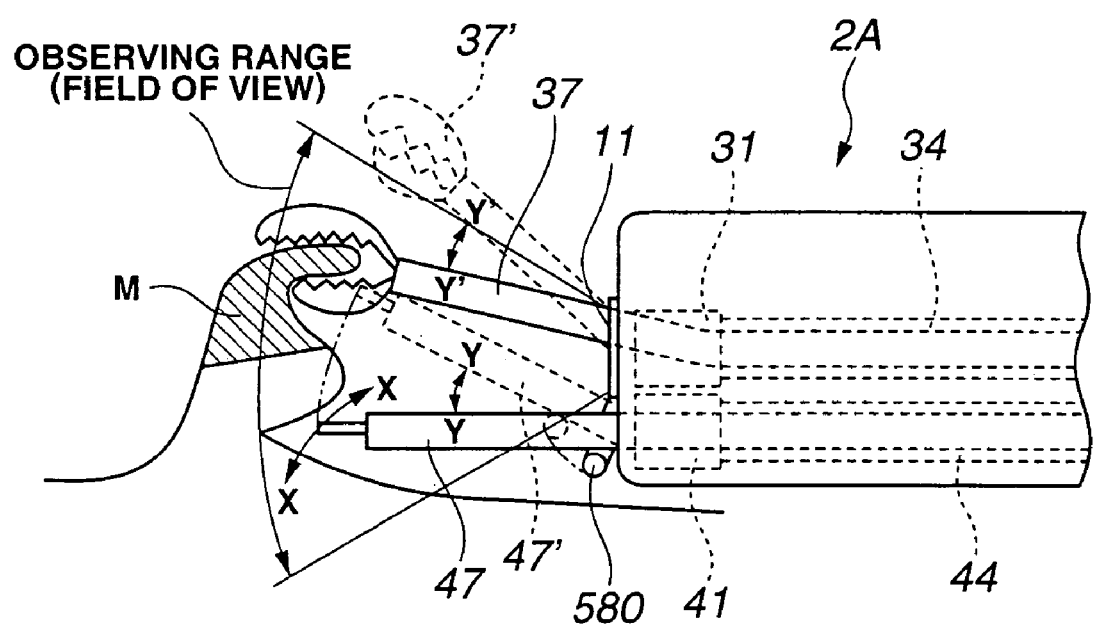
FIG. 24 is an explanatory diagram of the treatment operation of first and second treatment-tools in the endoscope apparatus according to the eighth embodiment.

FIGS. 22 to 24 relate to the eighth embodiment. FIG. 22 is a perspective view showing the entire structure of the endoscope apparatus. FIG. 23 is a plan view showing the edge portion of the inserting portion in the endoscope apparatus in the front view. FIG. 24 is an explanatory diagram of the treatment operation using the first and second treatment-tools in the endoscope apparatus.

A description is first given of the entire structure of an endoscope of the present invention with reference to FIG. 22. An endoscope apparatus 500A comprises an inserting portion 1A and an operating portion 506A. A universal cord 507 including a light guide cable and a signal cable is connected to the operating portion 506A.

The inserting portion 1A comprises, from the edge side, an edge portion 2A, a first bending portion 514, a second bending portion 513, and a flexible portion 512.

The observing window 11, the illuminating window 12, the air and water feed nozzle 14, and the front water-feed port 15 are arranged to the edge surface of the edge portion 2A. An almost L-shaped portion 613 for accommodating the treatment-tool oscillating base is formed to the edge surface of the edge portion 2A. The first treatment-tool oscillating base 31 and the second treatment-tool oscillating base 41 are oscillatably held in the portion 613 for accommodating the treatment-tool oscillating base.

The observing window 11 comprises an objective lens (not shown), and a solid image pick-up device for picking up an image of an observed portion. The solid image pick-up device is connected to the signal cable of the universal code 507. Light of the observed portion captured through the objective lens is guided to an eyepiece optical system (not shown) arranged to the operating portion 506A via an image guide cable (not shown) included in the operating portion 506A and the endoscope inserting portion 1A.

The universal code 507 is connected to a video processor device (not shown). The universal code 507 controls the driving of the solid image pick-up device, performs the signal processing of an image pick-up signal, records the image signal to a recording medium, and displays the picked-up image on a monitor.

Arranged to the illuminating window 12 are the endoscope inserting portion 1A, the operating portion 506A, and the end portion of a light guide cable (not shown) for guiding the illumination light included in the universal code 507. Illumination light from an illuminating device connected to the universal code 507 is guided by the light guide cable, and is projected to the observed portion.

The air and water feed nozzle 14 is continuously connected to an air and water feed channel (not shown) arranged to the operating portion 506A and the operating portion 1A. The air and water are fed to the observing window 11 by an air and water feed pump connected to the air and water feed channel.

The front water-feed port 15 is continuously connected to a front water feed channel (not shown) arranged to the operating portion 1A and the operating portion 506A, and is a jet orifice upon feeding water to the observed portion.

The first treatment-tool oscillating base 31 and the second treatment-tool oscillating base 41 are oscillated by the first oscillating base operating knob 519a and the second oscillating base operating knob 519b arranged to the operating portion 506A, which will be described later. The first treatment-tool oscillating base 31 is oscillated substantially in the vertical direction in the field of view, and the second treatment-tool oscillating base 41 is oscillated substantially in the horizontal direction in the field of view.

The first bending portion 514 is bent substantially in the vertical and horizontal directions in the field of view by the first bending portion 526 arranged to the operating portion 506A which will be described later.

The second bending portion 513 is bent substantially in the horizontal and vertical directions in the field of view by the second bending knob portion 528 arranged to the operating portion 506A, which will be described later.

The inserting portion 1A includes the first channel 34 for inserting the treatment tool and the second channel 44 for inserting the treatment tool.

The opening on the front side of the first channel 34 for inserting the treatment tool is continuously connected to the first treatment-tool oscillating base 31, and the opening on the rear side thereof is continuously connected to the first hole 521 for inserting the treatment tool arranged to the operating portion 506A.

The opening on the front side of the second channel 44 for inserting the treatment tool is continuously connected to the second treatment-tool oscillating base 41, and the opening on the rear side is continuously connected to the second hole 522 for inserting the treatment tool arranged to the operating portion 506A.

The operating portion 506A comprises an oscillating base operating portion 517A, the grip portion 520, the first bending portion 526, and the second bending knob portion 528.

The oscillating base operating portion 517A includes a first mechanism for operating the treatment-tool oscillating base and a second mechanism for operating the treatment-tool oscillating base (which are not shown). The first oscillating base operating knob 519a, as a part of the first mechanism for operating the treatment-tool oscillating base, arranged to the outside of the oscillating base operating portion 517A and the second oscillating base operating knob 519b as a part of the second mechanism for operating the treatment-tool oscillating base are arranged outside of the oscillating base operating portion 517A.

That is, the operation of the first oscillating base operating knob 519a remotely oscillates the first treatment-tool oscillating base 31 via the first mechanism for operating the treatment-tool oscillating base, substantially in the vertical direction. Further, the operation of the second oscillating base operating knob 519b remotely oscillates the second treatment-tool oscillating base 41 via the second mechanism for operating the treatment-tool oscillating base substantially in the horizontal direction. The oscillating operation of the first treatment-tool oscillating base 31 and the second treatment-tool oscillating base 41 will be described in detail later.

The outer surface of the oscillating base operating portion 517A has a front water-feed injecting port 623 and a cleaning port 624 of the oscillating base operating wire. The front water-feed injecting port 623 is continuously connected to the front water-feed port 15 arranged to the edge portion 2A via the water feed channel arranged in the endoscope inserting portion 1A. The cleaning port 624 of the oscillating base operating wire is continuously connected to the portion 613 for accommodating the treatment-tool oscillating base of the edge portion 2A via an operating wire inserting channel 560, which will be described later, arranged to the endoscope inserting portion 1A. A syringe (not shown) is connected to the cleaning port 624 of the oscillating base operating wire so as to feed the cleaning solution or the like to the operating wire inserting channel 560.

The first bending knob portion 526 externally has the vertical-operating knob 527a for the first bending portion, the horizontal-operating knob 527b for the first bending portion, the first vertical-rotating/fixing lever 529, and the first horizontal-rotating/fixing knob 530.

The vertical-operating knob 527a for the first bending portion is an operating knob which bends the first bending portion 514 in the vertical direction, and is connected to a vertical-operating wire (not shown) connected to the first bending portion 514 in the grip portion 520 or the first bending knob portion 526.

The horizontal-operating knob 527b for the first bending portion is an operating knob which bends the first bending portion 514 in the horizontal direction, and is connected to a horizontal-operating wire (not shown) connected to the first bending portion 514 in the grip portion 520 or the first bending knob portion 526.

The bending and the fixing of the first bending portion 514 through the vertical-operating knob 527a for the first bending portion are switched by the first vertical-rotating/fixing lever 529. The bending and fixing of the first bending portion 514 through the horizontal-operating knob 527b for the first bending portion are switched by the first horizontal-rotating/fixing knob 530.

The second bending knob portion 528 externally comprises the second bending knob 528a, and the second rotating/fixing knob 531.

The second bending knob 528a is a knob which bends the second bending portion 513 in the vertical direction, and is connected to a vertical-operating wire (not shown) connected to the second bending portion 513 in the grip portion 520 or the second bending knob portion 528.

The bending and the fixing of the second bending portion 513 through the second bending knob 528a are switched by the second rotating/fixing knob 531.

The button 523 for controlling the feed of air and water, the suction control button 524, and the image recording button 525 are arranged near the first bending knob portion 526.

The button 523 for controlling the feed of air and water is a button which drives and controls the air and water feed pump connected to the air and water feed nozzle 14 arranged to the edge portion 2A in the endoscope inserting portion 1A. The suction control button 524 is a button which drives and controls a pump for absorbing air and solution which are fed from the air and water feed nozzle 14, via an absorbing channel arranged to the edge portion 2A of the inserting portion 1A from the operating portion 506A (not shown). The image recording button 525 is a button which controls the image displayed on the monitor via a video processor connected to the universal cord 507, and the contents thereof are not described because they are not directly related.

At the connecting portion of the inserting portion 1A connected to the operating portion 506A, the bending preventing portion 516 is arranged. At the connecting portion of the universal code 507 connected to the operating portion 506A, a member 642 for preventing the crack of universal cord is arranged. The crack of the endoscope inserting portion 1A and the base portion of the universal code 507 is prevented.

Next, a description is given of the structure of the edge of the edge portion 2A with reference to FIG. 23. The observing window 11 is arranged in the center of the edge front side of the edge portion 2A. The illuminating window 12 is arranged to the right side of the observing window 11 in FIG. 23. The air and water feed nozzle 14 is arranged to the top side in FIG. 23. The front water-feed port 15 is arranged between the illuminating window 12 and the air and water feed nozzle 14.

An almost L-shaped portion 613 for accommodating the treatment-tool oscillating base is arranged from the left side to the bottom side of the observing window 11 in FIG. 23.

The portion 613 for accommodating the treatment-tool oscillating base positioned on the bottom side of the observing window 11 in FIG. 23 has the first treatment-tool oscillating base 31. The portion 613 for accommodating the treatment-tool oscillating base positioned on the left side of the observing window 11 in FIG. 23 has the second treatment-tool oscillating base 41.

The first treatment-tool oscillating base 31 and the second treatment-tool oscillating base 41 have a first treatment-tool inserting hole 646 and a second treatment-tool inserting hole 645, respectively.

The first treatment-tool inserting hole 646 and the second treatment-tool inserting hole 645 are connected to an opening 644 of the first channel 34 for inserting the treatment tool (shown by a dotted line in FIG. 23) and an opening 643 of the second channel 44 for inserting the treatment tool (shown by a dotted line in FIG. 23).

The second treatment-tool oscillating base 41 has a stand-up bar 580 which is substantially L-shaped. The base end of the stand-up bar 580 is fixed to the first treatment-tool oscillating base 31, and the front end side thereof is extended to the bottom side of a second treatment-tool inserting hole 645 in FIG. 23.

Operating wire inserting channels 560 are arranged near both ends of the first treatment-tool oscillating base 31 and the second treatment-tool oscillating base 41.

The operation of the second treatment-tool oscillating base 41 is the same as that according to the first embodiment as shown in FIG. 4. That is, the second treatment tool 47 inserted to the second channel 44 for inserting the treatment tool is guided or is projected to the outside from the edge portion 2A via the second channel opening portion 45 of the second treatment-tool oscillating base 41 from the opening of the second channel 44 for inserting the treatment tool.

The second rotating shaft 46 is arranged in the center of the second treatment-tool oscillating base 41. Terminal ends of the second operating wire 42 and the third operating wire 43 inserted to the operating wire inserting channel 560 are fixed and are connected to both ends of the second treatment-tool oscillating base 41 by using wire terminal members.

The base ends of the second operating wire 42 and the third operating wire 43 are connected and are fixed to the second oscillating base operating knob 519b via the first mechanism for operating the treatment-tool oscillating base of the oscillating base operating portion 517A.

That is, the rotation of the second oscillating base operating knob 519b stretches the second operating wire 42 and the third operating wire 43, thereby rotating the second treatment-tool oscillating base 41 in the horizontal direction with the second rotating shaft 46 as center. The rotation of the second treatment-tool oscillating base 41 oscillates the second treatment tool 47 inserted to the second treatment-tool inserting hole 645 in the horizontal direction.

The operation of the first treatment-tool oscillating base 31 is similar and a detailed description thereof is omitted here.

The second treatment tool 47 projected via the second treatment-tool inserting hole 645 of the second treatment-tool oscillating base 41 is oscillated in the range of the field of view for observation in the endoscope image. As shown in FIG. 23, the observing window 11 is arranged to the top side of the second treatment-tool oscillating base 41.

Next, a description is given of the operation of the endoscope apparatus using the first and second treatment-tools using the endoscope apparatus 500A with reference to FIG. 24.

Referring to FIG. 24, an incision clamp is inserted to the second treatment tool 47 inserted to the second treatment-tool oscillating base 41. The first treatment tool 37 which is inserted to the first treatment-tool oscillating base 31 is a grip clamp.

A lesion mucous membrane M is gripped by the grip clamp as the first treatment tool 37. Further, the first treatment-tool oscillating base 31 is operated, thereby oscillating the second treatment tool 47 in a Y-Y direction in FIG. 24 by the stand-up bar 580, and thereby oscillating the first treatment tool 37 in a Y'-Y' direction in FIG. 24. The second treatment tool 47 and the first treatment tool 37 are oscillated at the positions of a second treatment tool 47' and a first treatment tool 37' as shown by a dotted line in FIG. 24.

In other words, the lesion mucous membrane M gripped by the first treatment tool 37 is taken up in the upper direction in FIG. 24, and the incision clamp as the second treatment tool 47 is inserted into the bottom of the taken-up lesion mucous membrane M.

In this state, the second treatment-tool oscillating base 41 is oscillated in an X-X direction in FIG. 24 and, then, the incision operation of the lesion mucous membrane M starts. The incision of the lesion mucous membrane M is performed with accuracy and ease.

The length of the stand-up bar 580 is set to be shorter and then the second treatment tool 47 can be oscillated in the vertical direction by the stand-up bar 580 (first treatment-tool oscillating base 31) only upon oscillating the second treatment tool 47 on the rightmost. That is, the oscillating range of the second treatment tool 47 can be set depending on a length L of the stand-up bar 580.

At least one treatment tool is oscillated in four directions of the vertical and horizontal directions and the efficiency for treatment using the endoscope is improved. Further, advantageously, the inserting portion of the endoscope apparatus can be made thinner.

Ninth Embodiment

Figure 25:
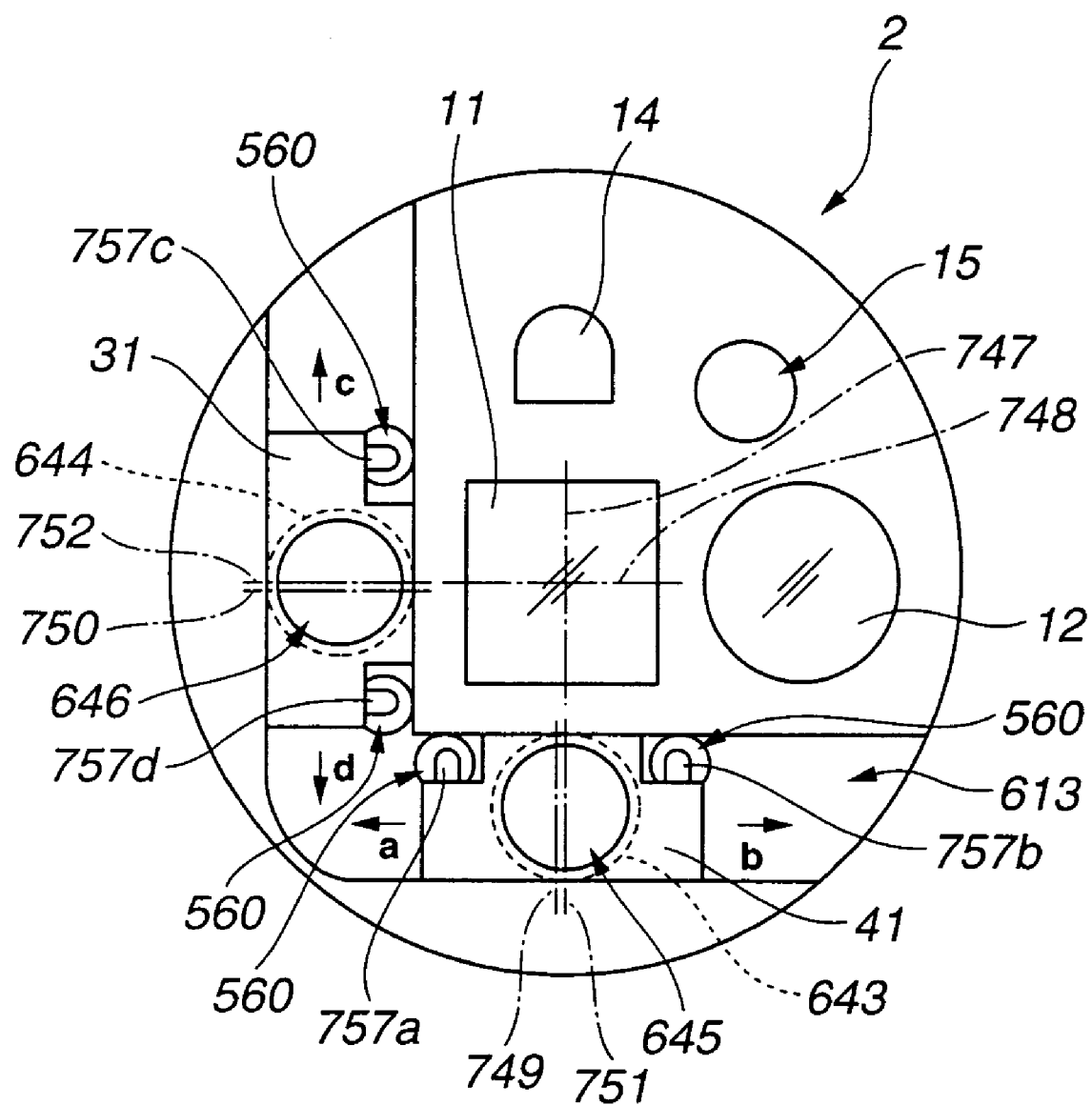
FIG. 25 is a front view showing an edge portion of an endoscope apparatus for explaining the structure of an edge surface thereof according to a ninth embodiment of the present invention.
Figure 26:
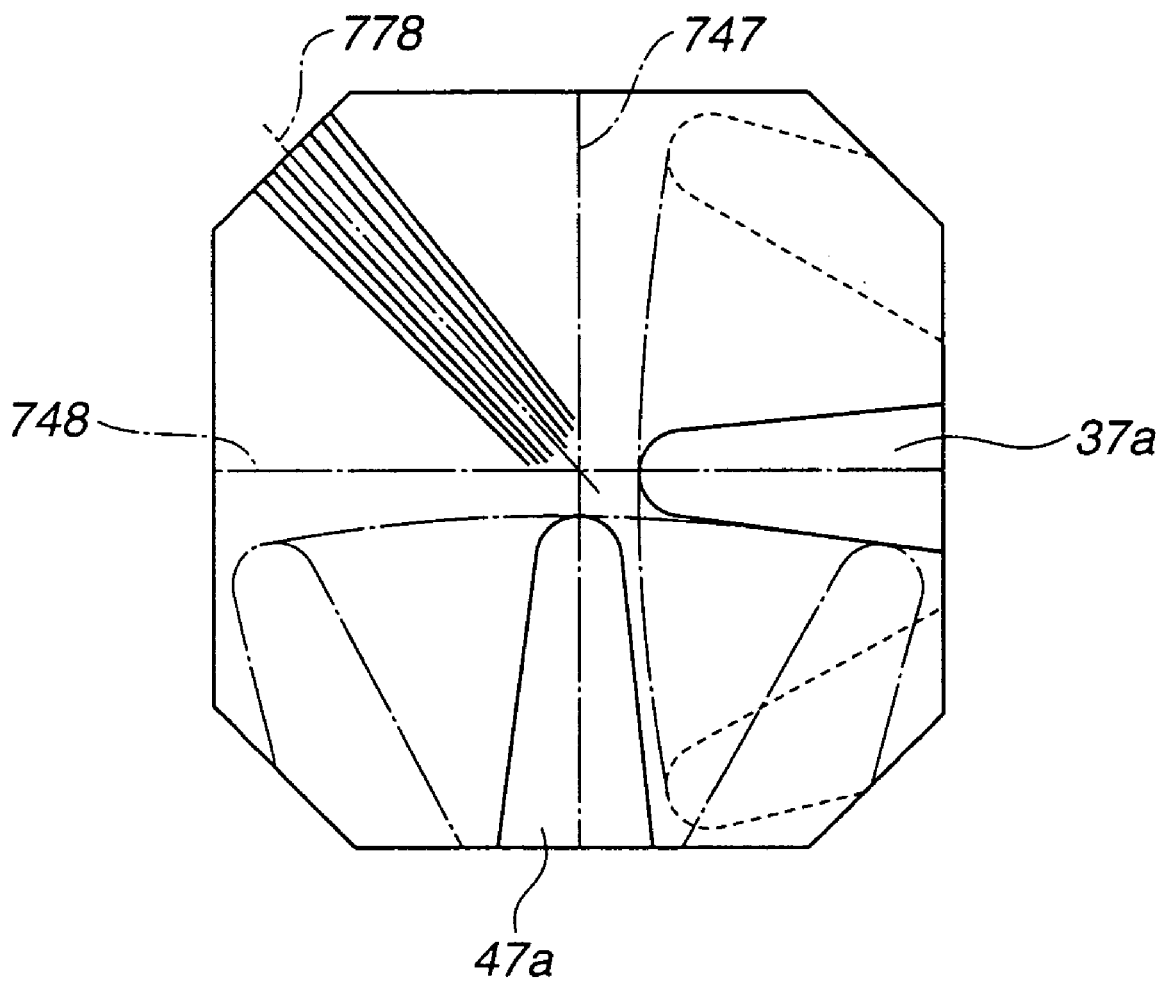
FIG. 26 is a diagram for explaining a first treatment-tool image or the like which is oscillated in an endoscope image according to the ninth embodiment.

FIGS. 25 and 26 relate to the ninth embodiment of the present invention. FIG. 25 is a front view showing an edge portion of an endoscope apparatus for explaining the structure of an edge surface thereof. FIG. 26 is a diagram for explaining a first treatment-tool image or the like for oscillating an endoscope image. The same portions as those according to the first to eighth embodiments are designated by the same reference numerals.

Referring to FIG. 25, the second treatment-tool oscillating base 41 has the second treatment-tool inserting hole 645 which is connected to a second opening 643 of the second channel 44 for inserting the treatment tool (shown by the broken line in FIG. 22). Reference numeral 749 denotes a center line of the second opening 643. A one-dotted line shown in reference numeral 751 denotes a center line of the second treatment-tool inserting hole 645 which is substantially perpendicular to the oscillating direction of the second treatment-tool oscillating base 41.

The first treatment-tool oscillating base 31 has the first treatment-tool inserting hole 646 which is continuously connected to a first opening 644 of the first channel 34 for inserting the treatment tool (shown by a broken line in FIG. 22). Reference numeral 750 denotes a center line of the first opening 644. A one-dotted line shown by reference numeral 752 is a center line of the second treatment-tool inserting hole 645 which is substantially perpendicular to the oscillating direction of the first treatment-tool oscillating base 31.

Reference numeral 747 denotes a center line on the observing window 11 in the horizontal direction as the center line which is equally sectioned on the endoscope image. Reference numeral 748 denotes a center line on the observing window 11 in the vertical direction which is equally sectioned on the top and the bottom of the endoscope image.

A position of an oscillating neutral state or, simply, oscillating neutral state in which the second and first treatment-tool oscillating bases 41 and 31 are not oscillated indicates a state in which the second inserting-hole center line 751 and the second opening-portion center line 749 are on substantially the same line and a state in which the first inserting-hole center line 752 and the first opening-portion center line 750 are on substantially the same line.

When the second treatment-tool oscillating base 41 is in the oscillating neutral state, a second inserting-hole center line 751 and a center line 747 in the horizontal direction are substantially on a single line, and the second treatment-tool oscillating base 41 is arranged to the observing window 11. When the first treatment-tool oscillating base 31 is in the oscillating neutral state, a first inserting-hole center line 752 and a center line 748 in the vertical direction are substantially on a single line, and the first treatment-tool oscillating base 31 is arranged to the observing window 11. That is, when the second treatment-tool oscillating base 41 and the first treatment-tool oscillating base 31 are arranged as shown in FIG. 25, the second treatment-tool oscillating base 41 and the first treatment-tool oscillating base 31 are in the oscillating neutral state.

The second treatment tool 47 and the first treatment tool 37 are guided from the second treatment-tool oscillating base 41 and the first treatment-tool oscillating base 31, respectively, and, as shown in FIG. 26, the endoscope image then indicates both a treatment-tool image 47a of the second treatment tool 47 which is guided from the second treatment-tool oscillating base 41, is projected from the lower side of the endoscope image, and is oscillated in the horizontal direction on the screen and a treatment-tool image 37a of the first treatment tool 37 which is guided from the first treatment-tool oscillating base 31, is projected from the right of the endoscope image, and is oscillated in the vertical direction on the screen. The treatment-tool images 47a and 37a shown by solid lines in FIG. 26 indicate the second treatment tool 47 and the first treatment tool 37 which are in the oscillating neutral state.

When the second treatment-tool oscillating base 41 and the first treatment-tool oscillating base 31 are in the oscillating neutral state, the second treatment tool 47 is near a center line 747 in the horizontal direction and the first treatment tool 37 is near a center line 748 in the vertical direction. Note that reference numeral 778 is the locus of the front water-feed passing near the center of the field of view.

The two treatment tools are guided from the treatment-tool oscillating base in the oscillating neutral state, thereby oscillating the treatment tools both in the stand-up direction and in the inverse direction. Further, the treatment-tool images are displayed toward the center of the image from the center in the horizontal direction and from the center in the vertical direction of the endoscope image. Therefore, the lesion portion is positioned in the center of the screen for the observation using the endoscope and for the treatment. Thus, the treatment tool smoothly approaches the lesion portion in the best direction and the operation is executed by oscillating the treatment tool without feeling that something is wrong while observing the endoscope image. As a result, the operability and the workability are extremely improved.

Tenth Embodiment

Figure 27:
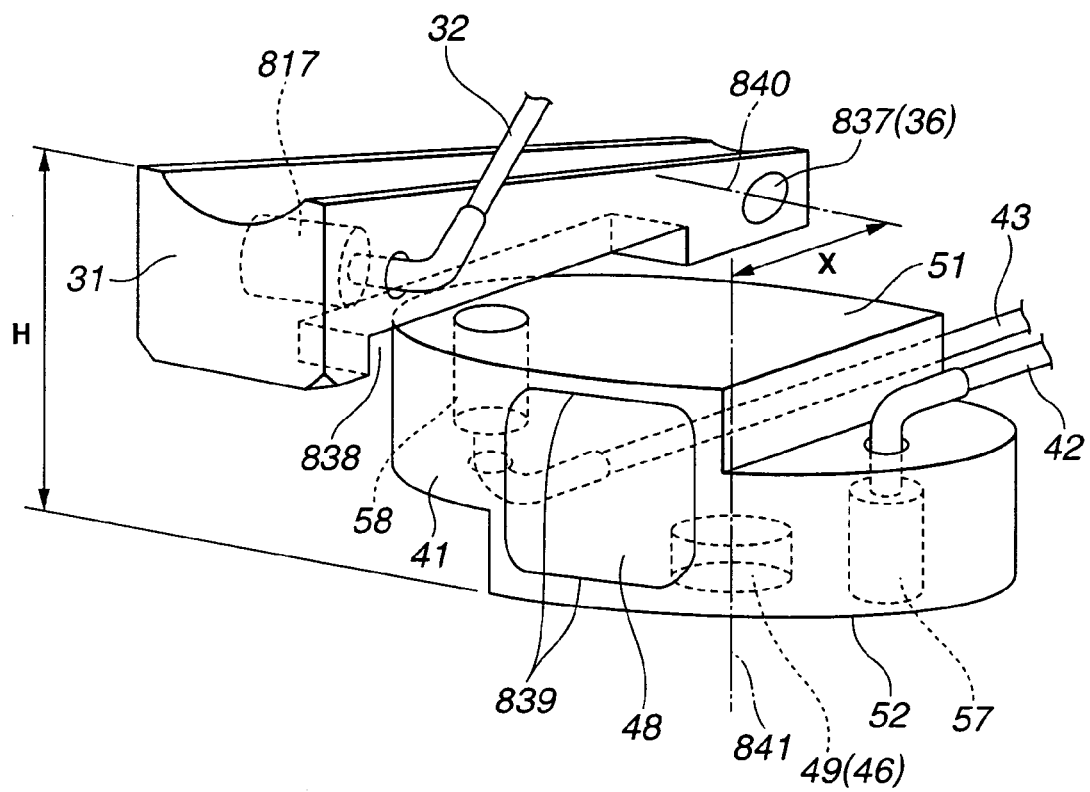
FIG. 27 is a perspective view showing first and second treatment-tool oscillating bases in an endoscope apparatus according to a tenth embodiment of the present invention.

FIG. 27 is a perspective view showing the first and second treatment-tool oscillating bases in an endoscope apparatus according to the tenth embodiment. The same portions as those according to the first embodiment are designated by the same reference numerals.

Although not shown, an endoscope according to the tenth embodiment comprises an elongated and soft inserting portion which is inserted in the living body and an operating portion arranged to the base end of the inserting portion. The inserting portion comprises, from the edge side, an edge portion, a bending portion, and a flexible portion. The operating portion is arranged to the base end of the flexible portion. The operating portion comprises a bending mechanism for operating the bending portion, a treatment-tool inserting hole, a mechanism for stand-up of the treatment tool, and a universal cord including a light guide and a signal cable.

Next, a description is given of the appearance and the arrangement relationship between the first treatment-tool oscillating base 31 and the second treatment-tool oscillating base 41 with reference to FIG. 27.

The first treatment-tool oscillating base 31 is entirely rect-angular-parallelepiped, and the edge of the first operating wire 32 is rotatably attached to the edge of the first treatment-tool oscillating base 31 via a first wire-terminal member 817. The first operating wire 32 is inserted between the first treatment-tool oscillating base 31 and the observing window 11 (refer to FIG. 1), and is attached to the first wire-terminal member 817 from the side surface of the second treatment-tool oscillating base 41. On the hand side of the first treatment-tool oscillating base 31, a first rotating-shaft, hole 837 having the first rotating shaft 36 is arranged. That is, the first operating wire 32 is stretched and then the first treatment-tool oscillating base 31 is rotated in the upper direction in FIG. 27 with the first rotating-shaft hole 837 as center.

A caved portion 838 is formed at a part of the bottom of the first treatment-tool oscillating base 31 so as to prevent the collision and interference with the second treatment-tool oscillating base 41. A caved surface is formed in the longitudinal direction of the top surface so that the first treatment tool 37 is inserted and is placed and it is easily oscillated and guided. An overlap height H between the first treatment-tool oscillating base 31 and the second treatment-tool oscillating base 41 is reduced by the caved portion 838, and the edge portion 2 of the endoscope inserting portion 1 has a thinner diameter.

The second treatment-tool oscillating base 41 is entirely cylindrical, partly including a cut portion of an arcuate portion. The treatment tool inserting portion 48 is formed so as to insert the second treatment tool 47 in the diameter direction from the side surface of the cut portion of the arcuate portion. In the center of the lower surface 52 of the second treatment-tool oscillating base 41, the second rotating shaft hole 49 is formed for inserting the second rotating shaft 46.

The upper surface 51 and the lower surface 52 of the second treatment-tool oscillating base 41 have notch surfaces arranged in different directions. The edges of the second operating wire 42 and the third operating wire 43 are rotatably attached to the notch surfaces via the wire end member 57 and the wire end member 58.

In other words, when the first operating wire 42 and the second operating wire 43 are operated, they are rotated in the horizontal direction in FIG. 27 with the second rotating shaft hole 49 as center. The second treatment-tool oscillating base 41 may be rotated by a single operating wire, except for using the above-mentioned two operating wires (second operating wire 42 and third operating wire 43).

The two surfaces of the upper surface 51 and the lower surface 52 of the second treatment-tool oscillating base 41 are slid as sliding surfaces with the edge constructing portion 10. Although the material of the upper surface 51 and the lower surface 52 is not particularly limited, it is preferable to use a material with excellent causticity and moisture resistance.

The shape of opening of the treatment tool inserting portion 48 is rectangular with an edge-line portion 839 which is substantially in parallel with the upper surface 51 and the lower surface 52 as the sliding surfaces, as shown in FIG. 27. Not the edge line but the surface may be arranged near the opening portion on the edge side.

A first rotating-shaft center 840 of the first treatment-tool oscillating base 31 is a center of the first rotating shaft 36 attached to the first rotating-shaft hole 837, and a second rotating-shaft center 841 of the second treatment-tool oscillating base 41 is a center of the second rotating shaft 46 attached to the second rotating shaft hole 49. As shown in FIG. 27, with respect to a positional relationship between the first rotating-shaft center 840 and the second rotating-shaft center 841, the second rotating-shaft center 841 is arranged near the edge side in the longitudinal direction by a distance X, as compared with the arrangement of the first rotating-shaft center 840.

According to the tenth embodiment, referring to FIG. 27, the overlap height H between the first treatment-tool oscillating base 31 and the second treatment-tool oscillating base 41 is reduced by the caved portion 838 and the edge portion 2 of the endoscope inserting portion 1 has a thinner diameter. The second rotating-shaft center 841 of the second rotating shaft 46 in the second treatment-tool oscillating base 41 is arranged near the edge side in the longitudinal direction as compared with the arrangement of the first rotating-shaft center 840 of the first rotating shaft 36 in the first treatment-tool oscillating base 31 arranged to the edge portion 2. Thus, the edge portion 2 has a thinner diameter and the oscillating guiding range of the second treatment tool 47 is widened.

As mentioned above, in the endoscope apparatus of the present invention, since the first treatment-tool is adjusted to be out of the field of view, the workability is improved upon the treatment using the endoscope by projecting the treatment tools from the edge openings of at least two channels for inserting the treatment tool. Further, the conventional troublesomeness that the two treatment tools are viewed in the narrow image pick-up screen is solved and the observing property of the lesion portion is improved. Furthermore, since the touching state of the two treatment tools is prevented, the operation using the treatment tool is smooth and the workability is improved.

In addition, in the endoscope apparatus of the present invention, the treatment-tool oscillating base is arranged near the opening portion of the channel for inserting the treatment tool and the treatment tool is maximally oscillated by the treatment-tool oscillating base. Then, the sandwiching of the treatment tool is prevented and the treatment tool easily advances or returns and is inserted in the longitudinal direction. The edge portion is formed with small size while treatment tool is exchanged fast. Consequently, the operating efficiency of the treatment using the endoscope is improved and, advantageously, the burden on the operator or patient is reduced.

In addition, in the endoscope apparatus of the present invention, the member for transmitting the treatment-tool oscillating base can be accommodated in the cylindrical structure of the operating portion of the grip portion in the operating portion. Since the mechanism for operating the treatment-tool oscillating base and the grip portion are deviated to the inserting portion side and are detached, this facilitates the work for removing and adjusting the loosing of the bending wire in the connecting portion between the bending wire and the bending mechanism and this further improved the efficiency.

Having described the preferred embodiments of the invention referring to the accompanying drawings, it should be understood that the present invention is not limited to the those precise embodiments and various changes and modifications thereof could be made by one skilled in the art without departing from the spirit or scope of the invention as defined in the appended claims.

What is claimed is:

1. An endoscope apparatus comprising:
an insertion portion having first and second channels arranged therein and terminating at first and second openings, respectively, at a distal portion of the insertion portion;
an observation optical system for capturing an observation image, which is arranged to the insertion portion;
a first treatment-tool oscillating base which guides, in a first direction and centering around a first rotating shaft, a first treatment-tool inserted via the first channel arranged to the insertion portion, a range of oscillation of the first treatment-tool by the first treatment-tool oscillating base being set so as to cause a distal end of the first treatment-tool to be selectively positioned inside or outside the observation image; and
a second treatment-tool oscillating base which guides, in a second direction which is different from the first direction and centering around a second rotating shaft, a second treatment-tool inserted via the second channel arranged in the insertion portion, the second rotating shaft being positioned closer to the distal portion side of the insertion portion than the first rotating shaft.

2. An endoscope apparatus according to claim 1, wherein an oscillating range of the second treatment-tool oscillating base is wider than an oscillating range of the first treatment-tool oscillating base.

3. An endoscope apparatus according to claim 2, wherein a distance from the first rotating shaft to a distal end of the first treatment-tool oscillating base is greater than a distance from the second rotating shaft to a distal end of the second treatment-tool oscillating base.

4. An endoscope apparatus according to claim 3, wherein
the first treatment-tool oscillating base oscillates the first treatment-tool centering around the first rotating shaft in an essentially vertical direction on the observation image, and
the second treatment-tool oscillating base oscillates the second treatment-tool centering around the second rotating shaft in an essentially horizontal direction on the observation image.

5. An endoscope apparatus according to claim 4, wherein the oscillating range of the second treatment-tool by the second treatment-tool oscillating base is set in a range that a distal end of the second treatment-tool is positioned within a length in the horizontal direction of the observation image.

6. An endoscope apparatus according to claim 5, further comprising a display apparatus which displays the observation image,
wherein the observation image displayed by the display apparatus has a screen size with a length in the horizontal direction longer than that in the vertical direction.

7. An endoscope apparatus according to claim 6, wherein the first and second treatment-tool oscillating bases are rotatably provided in respective openings of the first and second channels, respectively.

8. An endoscope apparatus according to claim 1, wherein an oscillating range of the first treatment-tool by the first treatment-tool oscillating base is set outside an oscillating range of the second treatment-tool by the second treatment-tool oscillating base.

* * * * *